(12) United States Patent
Atala et al.

(10) Patent No.: US 7,429,490 B2
(45) Date of Patent: Sep. 30, 2008

(54) TISSUE ENGINEERED UTERUS

(75) Inventors: Anthony Atala, Winston Salem, NC (US); James J. Yoo, Brookline, MA (US)

(73) Assignee: Children's Medical Center, Boston, MA (US)

( * ) Notice: Subject to any disclaimer, the term of this patent is extended or adjusted under 35 U.S.C. 154(b) by 250 days.

(21) Appl. No.: 11/052,459

(22) Filed: Feb. 7, 2005

(65) Prior Publication Data

US 2005/0208026 A1 Sep. 22, 2005

Related U.S. Application Data

(62) Division of application No. 10/295,812, filed on Nov. 15, 2002, now Pat. No. 7,049,057.

(60) Provisional application No. 60/331,503, filed on Nov. 16, 2001.

(51) Int. Cl.
*C12N 5/06* (2006.01)
*C12N 5/08* (2006.01)
*A61F 2/04* (2006.01)

(52) U.S. Cl. .................. 435/373; 435/1.1; 623/23.64

(58) Field of Classification Search .................. 435/1.1
See application file for complete search history.

(56) References Cited

U.S. PATENT DOCUMENTS

| 5,266,480 | A | 11/1993 | Naughton et al. |
| 5,567,612 | A | 10/1996 | Vacanti et al. |
| 5,770,193 | A | 6/1998 | Vacanti et al. |
| 5,851,833 | A | 12/1998 | Atala |
| 5,855,610 | A | 1/1999 | Vacanti et al. |
| 5,863,531 | A | 1/1999 | Naughton et al. |
| 6,576,019 | B1 | 6/2003 | Atala |
| 7,049,057 | B2 | 5/2006 | Atala |
| 2003/0166274 | A1 | 9/2003 | Hewitt |

FOREIGN PATENT DOCUMENTS

| WO | WO 99/22781 | 5/1999 |
| WO | 99/62426 | 12/1999 |
| WO | WO 99/62425 | 12/1999 |

OTHER PUBLICATIONS

Cooke et al. "Restoration of normal morphology and estrogen responsiveness in cultured vaginal and uterine epithelia transplanted with stroma". Proc. Natl. Acad. Sci. USA. Apr. 1986. vol. 83, pp. 2109-2213.*
Cima, L.G. et al., *J. of Biomed. Engineering*, 113:143-151 (1991).
Park, K.D. et al., *Yonsei Medical Journal*, 41(6):780-788 (2000).
Yoo, J. et al., *Yonsei Medical Journal*,41(6):789-802 (2000).
Glasser et al., *J. of Cell Biology*, 107(6 Pt. 1):2409-2423 (1988).
Doillon, et al., "Method of Growing Vaginal Mucosal Cells on a Collagen Sponge Matrix" The Journal of Reproductive Medicine, vol. 35, No. 3, Mar. 1990, pp. 203-207.
Marieb, The Benjamin/Cummings Publishing Company, second edition, 1992. "Human Anatomy & Physiology".
Matapurkar, Indian Journal of Experimental Biology, 2000, 38:129-136. "Organogenesis and tissue regeneration of fallopian tube: A desired metaplastic transformation of mesodermal stem cells in live animal models (dogs)."

* cited by examiner

*Primary Examiner*—Vera Afremova
(74) *Attorney, Agent, or Firm*—Nixon Peabody LLP

(57) ABSTRACT

The invention is directed to compositions and methods for reconstructing artificial female reproductive organs. The constructs and methods of the invention can be used for ameliorating congenital malformations and disorders of female reproductive tract using tissue engineered female reproductive organs, such as the uterus, vagina, cervix, and fallopian tubes. These tissue engineered female reproductive organs can be generated by perfusing cultured cell populations derived from cells of the female reproductive tissues, such as uterine, vaginal, cervical, fallopian tube epithelial cells as well as smooth muscle cells.

7 Claims, 5 Drawing Sheets

TISSUE ENGINEERED UTERUS

Cross-Reference to Related Applications

The present invention is a Divisional Application of U.S. Ser. No. 10/295,812, filed Nov. 15, 2002, which claims benefit under 35 U.S.C 119(e) of U.S. Provisional Application No. 60/331,503, filed Nov. 16, 2001.

BACKGROUND OF THE INVENTION

The technical field of the present invention is tissue engineering, in particular, the construction of tissue engineered female reproductive organs. The invention is particularly useful in constructing tissue engineered vagina, fallopian tubes, uterus, and cervix.

A variety of pathological disorders exist, affecting the external genitalia and mandating extensive surgical intervention (Hendren, H. W. (1998). Cloacal malformations. In "Campbell's Urology" 7$^{th}$ ed., Saunders, Philadelphia, 1991-2001). Male genital reconstruction affords the most currently reported long term clinical success with tissue engineering applications and substantiated suitability for urethral reconstruction (Atala et al. *J. Urol.* 162: 1148-1151 (1999); Chen et al. *World J. Urol.* 18(1) 67-70 (2000)). Certainly other disorders like cloacal malformations and exstrophy can result in severe genital ambiguity for both male and females. However, there is a paucity of information regarding the reconstruction of female genitalia and vaginal reconstruction.

Congenital malformations of the vagina, cervix, and uterus have profound implications for gynecological patients. These anomalies are often detected in the adolescent period. For proper management, the physician requires a thorough understanding of normal embryology and sexual differentiation. Although clinical experience helps the gynecologist appreciate the disturbed anatomic configurations, each individual who presents with a defect must be thoroughly evaluated because genital tract aberrations do not necessarily follow any defined and consistent pattern. Examples of female genital abnormalities include ambiguous genitalia, vaginal and uterine atresia, obstructed outflow tract disorders, cervical atresia, urogenital sinus disorders, and virilization disorders (Edmonds, D. K., *Obstet Gynecol Clin North Am* 27(1):49-62 (2000)). Genital malformations can be particularly disturbing to the patient and her family because they not only have reproductive implications but also significant psychological and sexual overtones that need to be addressed and dealt with in a sensitive and reassuring manner. A more in depth discussion can be found in the textbooks (Rock J A "Surgery for anomalies of the mullerian ducts." In: *Te Linde's Operative Gynecology* (8th ed). Edited by J Rock, J. Thompson. Philadelphia, Lippincott-Raven, 1997; Edmonds D K: "Sexual development anomalies and their construction: upper and lower tracts." In: *Pediatric and Adolescent Gynecology*. Edited by J Sanfilippo, D Muram, P Lee, J Dewhurst. Philadelphia, W. B. Saunders, 1994; Jones H W Jr: "Construction of congenital uterovaginal anomalies." In: *Female Reproductive Surgery*. Edited by J Rock, A Murphy, H W Jones Jr. Baltimore, Williams & Wilkins, 1992).

Congenital and acquired uterine malformations, such as hypoplastic or a plastic uterine anomalies, tumor, trauma, and severe inflammatory diseases, account for a large percentage of female infertility. The options available for uterine reconstruction are limited. Pregnancy cannot be achieved if extrauterine tissues are used for reconstruction. Uterine tissue substitution has been tried experimentally using synthetic biomaterials, however, these attempts have not been successful, likely due to the complex physical and functional characteristics of the uterus (Jonkman et al. *Artif Organs,* 10: 475-80, 1986)).

Congenital female genital anomalies and cloacal malformations, such as icornuate/septate uterus, uterus didelphys, cervical and vaginal atresia, obstructed genital tract, may also require extensive surgical construction. Surgical challenges are often encountered due to the limited amount of native tissue available. Currently, non-reproductive tract tissues are being used for vaginal construction, despite a number of associated complications. These include treatment such as the transabdominal method of retroperitoneal sacropexy for the creation of sigmoid vagina, for example in a patient suffering from Mayer-Rokitansky-Kuster-Hauser syndrome. These creations however are prone to prolapse, resulting in a "falling-out" sensation in the vagina, pain, leukorrhea and dyspareunia, and necessitating repair. Other patients with, for example, agenesis of the vagina and cervix, but with a functional endometrium, are typically treated by the traditional treatment of hysterectomy with the subsequent construction of a neovagina. This requires a vaginal skin graft that may not heal well, and may also result in disturbances of menstruation.

Currently, the various procedures used for female reproductive organ reconstruction employ non-homologous tissue sources. However, the use of non-homologous tissue for female organ reconstruction is associated with limited functionality. Thus, there is a need in the art regarding the engineering of female reproductive and genital tissues that address the problems these problems.

Accordingly, a need exists for the generation of female reproductive organs using the autologous cells to produce reproductive tract organs and tissues.

SUMMARY OF THE INVENTION

The present invention provides compositions and methods for ameliorating congenital malformations and disorders of the female reproductive tract using tissue engineered female reproductive organs. These tissue engineered female reproductive organs can be generated by culturing cell populations derived from the cell of the reproductive tract tissues, such as vaginal epithelial, fallopian tube epithelial cells, cervical epithelial cells, uterine epithelial cells and smooth muscle cells. The cultured cells are perfused on or into a biocompatible matrix. The methods of the invention can be used to reconstruct female reproductive organs that include, but are not limited to, the cervix, uterus, vagina, and fallopian tubes.

The biocompatible matrix can be perfused with a population of female reproductive cells, e.g., uterine epithelial cells, vaginal epithelial cells, fallopian tube epithelial cells, and smooth muscle cells, e.g, myometrial cells, which develop into the respective reproductive tract tissue layers. Accordingly, in one aspect, the invention features a method of reconstructing an artificial female reproductive organ construct by perfusing a first population of cultured female reproductive cells into one side of a biocompatible matrix, such that the cultured female reproductive cells attach to the biocompatible matrix; culturing the cultured female reproductive cells in the biocompatible matrix until the cultured female reproductive cells produce a first female reproductive tissue layer; perfusing a second population of cultured female reproductive cells that are different from the first population of cultured female reproductive cells onto a second side of a biocompatible matrix, such that the second population of cultured female reproductive cells attach to the biocompatible matrix; and culturing the second population of cultured female reproductive cells in the biocompatible matrix until the cultured female reproductive tract cells produce a second female reproductive tissue layer that is different from the first reproductive tissue layer, to thereby create an female reproductive organ construct.

The artificial female reproductive organ construct can also be created by culturing the first and second populations of reproductive tract cells on the same side of the biocompatible matrix. In one embodiment, the female reproductive organ construct can be created by using one population of female reproductive cells, e.g., vaginal epithelial cells. In another embodiment, the female reproductive organ construct can be created by using at least two different populations of female reproductive cells, e.g., vaginal epithelial cells and smooth muscle cells. In other embodiments, the female reproductive organ construct can be created by using any number of different populations of female reproductive cells, e.g., three different populations or more. Also within the scope of the invention is a female reproductive organ construct created from at least one population of female reproductive cells and another population of cells that are not derived from the female reproductive, e.g., smooth muscle cells derived from the bladder.

In another aspect, the invention features a method of reconstructing an artificial uterus construct by perfusing a population of cultured uterine epithelial cells into one side of a biocompatible matrix, such that the uterine epithelial cells attach to the biocompatible matrix; culturing the uterine epithelial cells in biocompatible matrix until the epithelial cells produce a uterine epithelial tissue layer, e.g., endometrim; perfusing a population of cultured smooth muscle cells, e.g., myometrial cells, into a second side of a biocompatible matrix, such that the myometrial cells attach to the biocompatible matrix; and culturing the myometrial cells in the biocompatible matrix until the myometrial cells produce a myometrial tissue layer, to thereby create an artificial uterus. In another embodiment, the artificial uterus can be created by seeding cells on both sides of a biocompatible matrix. In another embodiment, the artificial uterus can be created by layering layers of cells, e.g., uterine epithelial cells can be seeded onto both sides of a biocompatible matrix followed by seeding of smooth muscle cells, e.g., myometrial cells. In yet another embodiment, uterine epithelial cells and smooth muscle cells can be seeded simultaneously onto a biocompatible matrix.

In yet another aspect, the invention features a method of reconstructing an artificial vagina construct by perfusing a population of cultured vaginal epithelial cells into one side of a biodegradable matrix, such that the vaginal epithelial cells attach to the biocompatible matrix; culturing the vaginal epithelial cells in the biocompatible matrix until the vaginal epithelial cells produce a vaginal epithelial tissue layer; perfusing a population of cultured smooth muscle cells into a second side of a biocompatible matrix, such that the smooth muscle cells attach to the biocompatible matrix; and culturing the smooth muscle cells in the biocompatible matrix until the smooth muscle cells produce a smooth muscle tissue layer, to thereby create an artificial vagina. In another embodiment, the artificial vagina can be created by seeding cells on both sides of a biocompatible matrix. In another embodiment, the artificial vagina can be created by layering layers of cells, e.g., vaginal epithelial cells can be seeded onto both sides of a biocompatible matrix followed by seeding of smooth muscle cells. In yet another embodiment, vaginal epithelial cells and smooth muscle cells can be seeded simultaneously onto a biocompatible matrix.

The biocompatible matrix can be composed of a non-degradable or a biodegradable material. The biocompatible matrix can form a three-dimensional scaffold. The biocompatible matrix may also be composed of decellularized organ material. When grown in this biocompatible matrix, the proliferating cells mature and segregate properly to form tissues analogous to counterparts found in vivo. In other embodiments, part of the female reproductive system is replaced by an artificial female reproductive organ.

In another aspect, the invention features a method of treating a subject with a reproductive disorder by implanting an artificial female reproductive organ formed by perfusing a first population of cultured female reproductive tract cells into one side of a biodegradable matrix, such that the cultured female reproductive tract cells attach to the biocompatible matrix; culturing the cultured female reproductive tract cells in the biocompatible matrix until the cultured female reproductive tract cells produce a first female reproductive tissue layer; perfusing a second population of cultured female reproductive tract cells that are different from the first population of cultured female reproductive tract cells onto a second side of a biocompatible matrix, such that the second population of cultured female reproductive tract cells attach to the biocompatible matrix; and culturing the second population of cultured female reproductive tract cells in the biocompatible matrix until the cultured female reproductive tract cells produce a second female reproductive tissue layer that is different form the first reproductive tissue layer; and monitoring the subject for a modulation in the reproductive organ disorder. The artificial female reproductive organ or tissue structure exhibits the compliance and vasculature of natural female reproductive organ. In one embodiment, the artificial female reproductive organ is an artificial vagina. In another embodiment, the artificial female reproductive organ is an artificial uterus. In another embodiment, the artificial female reproductive organ is an artificial cervix. In another embodiment, the artificial female reproductive organ is a fallopian tube.

In another aspect, the invention features an artificial female reproductive organ comprising a three-dimensional scaffold made of a biodegradable matrix, perfused with at least one population of cultured female reproductive tract cells that produce at least one female reproductive tissue layer to create an female reproductive organ construct. In another embodiment, the artificial female reproductive organ construct comprises at least two different populations of cultured female reproductive tract cells that produce at least two different female reproductive tissue layers. In one embodiment, the two different female reproductive tissue layers are produce on the same side of biodegradable matrix. In another embodiment, the two different female reproductive tissue layers are produced on two different sides of the biodegradable matrix. In another embodiment, the first and second cell populations are perfused into or on separate matrix layers and the matrix layers are combined after perfusion.

In another aspect, the invention features a method of screening for compounds that modulate female reproductive cells. The method involves providing an implantable, biocompatible matrix, which has been perfused with a female reproductive cell population and with smooth muscle cell population, such that the female reproductive cell population attaches to the muscle cell population forming a tissue structure having compliance of normal uterine tissue; contacting the artificial female reproductive organ with a library of test compounds; and selecting from the library of test compounds a compound of interest that modulates female reproductive cells. The compound may be a chemical or pharmaceutical agent which can be cytotoxic, therapeutic, affect implantation of an embryo, or modulate contraction.

DETAILED DESCRIPTION

Figure 1:
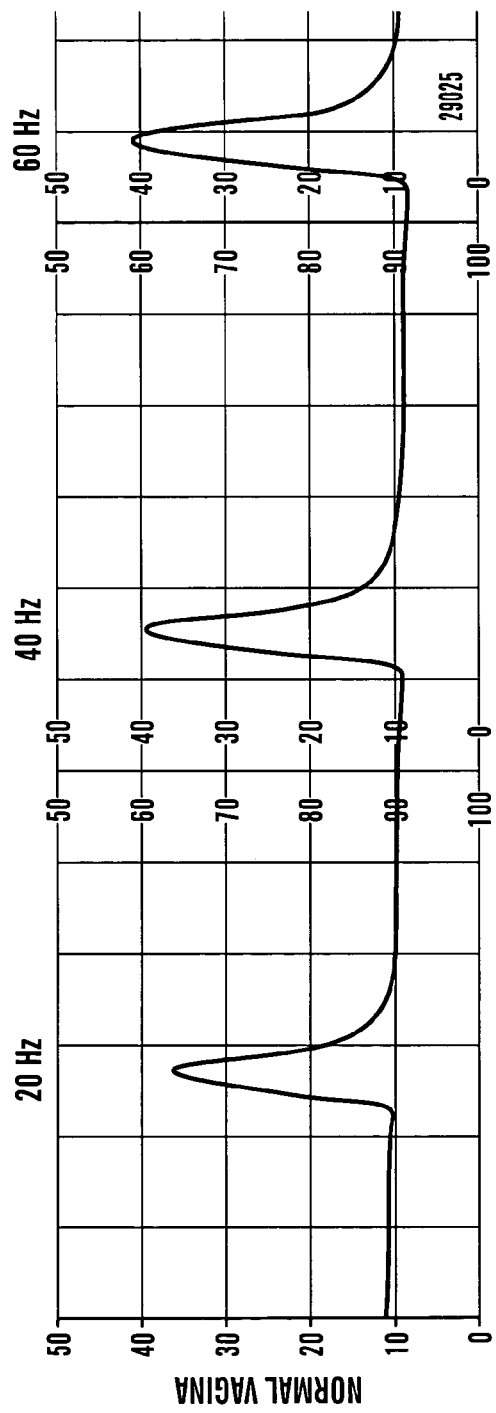
FIG. 1 is a graph demonstrating evoked potentials at various levels of electrical stimulation for both normal and tissue engineered (TE) vagina 6 weeks after implantation.
Figure 1:
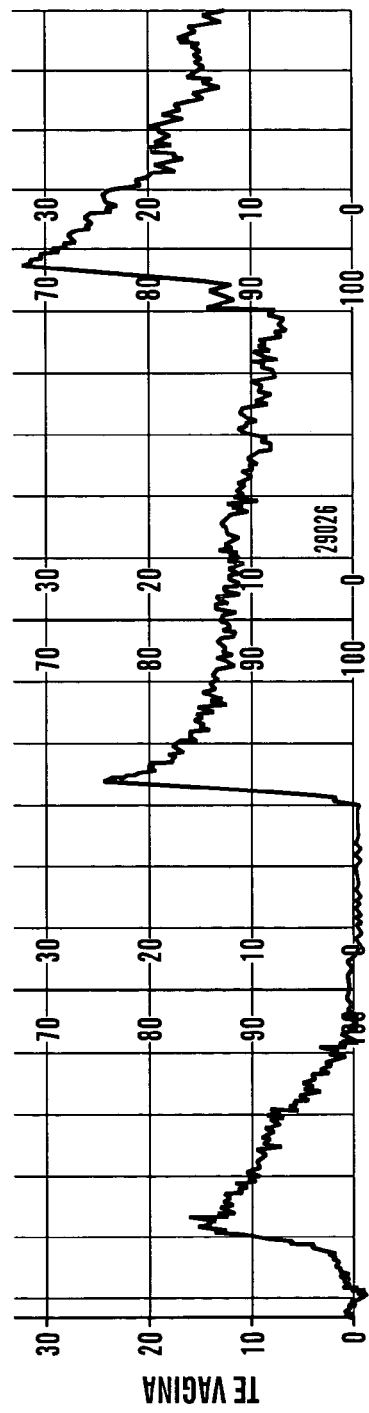
Figure 2A:
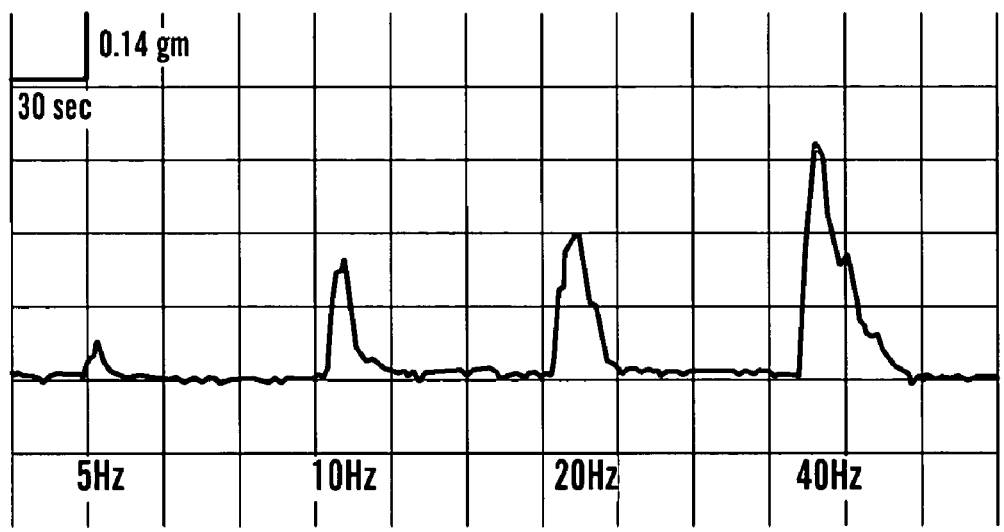
FIG. 2A is a graph depicting normal uterine tissue response to electrical field stimulation.
Figure 2B:
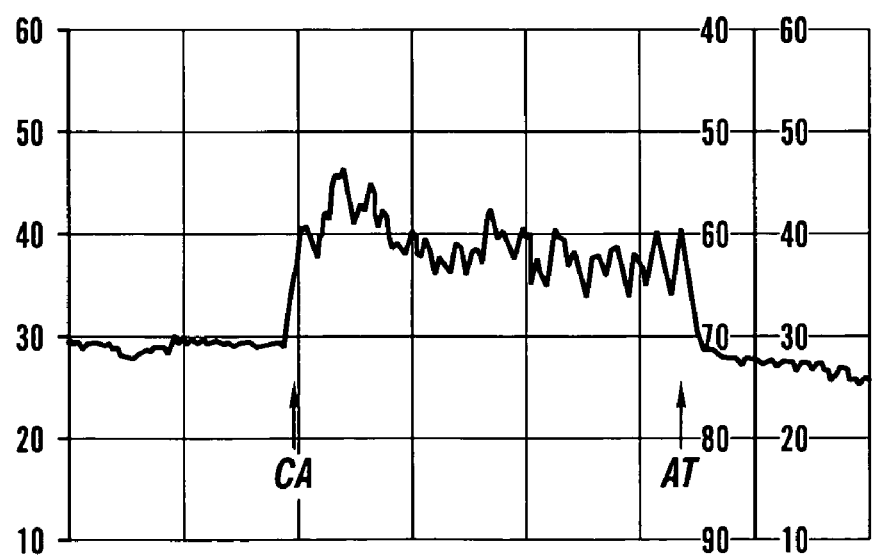
FIG. 2B is a graph depicting normal uterine tissue response to the pharmacological stimulation of carbachol (CA) and atropine (AT)
Figure 2C:
FIG. 2C is a graph depicting normal uterine tissue response to the pharmacological stimulation of phenylephrine (PE) and phentolamine (PL)
Figure 2D:
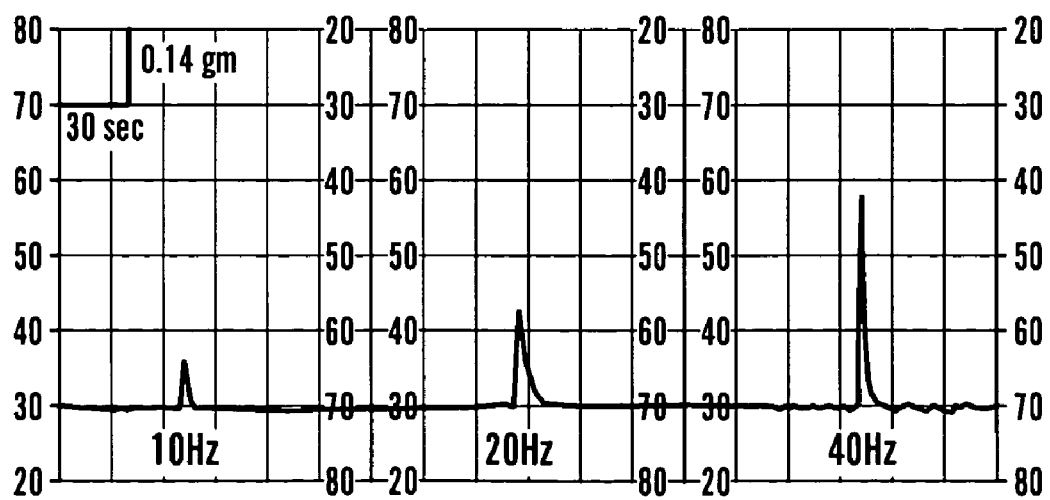
FIG. 2D is a graph depicting cell-seeded uterine implanted tissue response to electrical field stimulation (100 v; 1 ms)
Figure 2E:
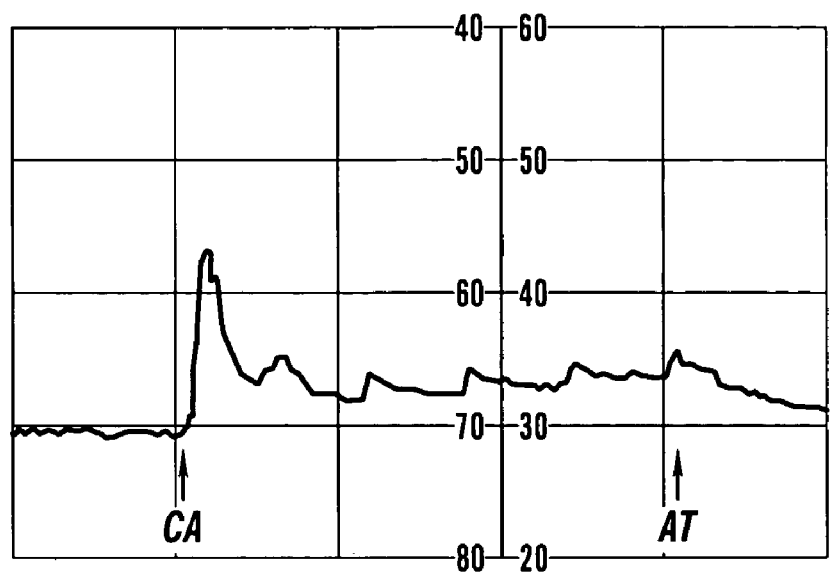
FIG. 2E is a graph depicting cell-seeded uterine implanted tissue response to the pharmacological stimulation of carbachol (CA) and atropine (AT)
Figure 2F:
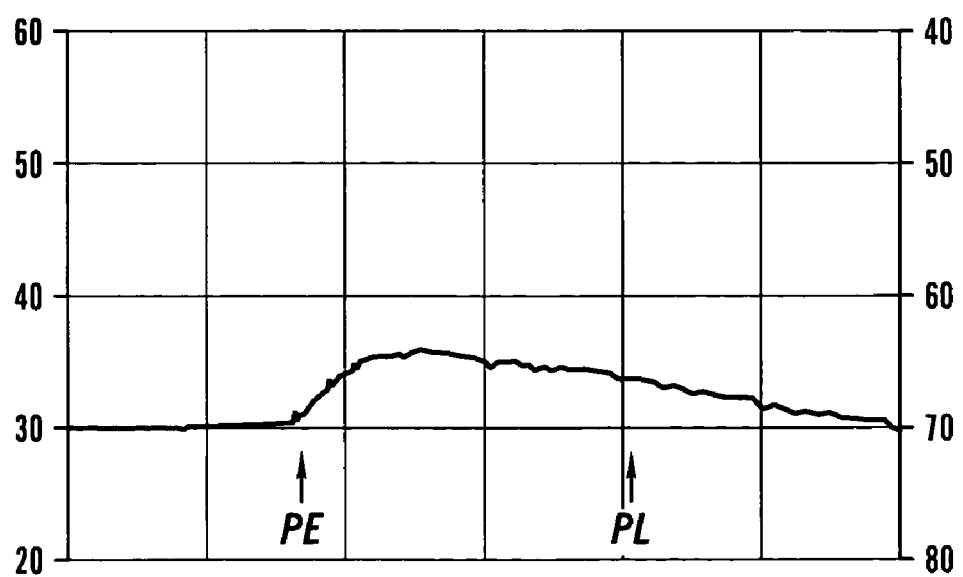
FIG. 2F is a graph depicting cell-seeded uterine implanted tissue response to the pharmacological stimulation of phenylephrine (PE) and phentolamine (PL)

The present invention is directed to the reconstruction, repair, augmentation or replacement of a female reproductive organ or tissue structures. The practice of the present invention employs methods of tissue engineering involving cell culture, cell expansion, cell seeding on biomatrices, and implantation of the constructs in vivo for tissue substitution.

So that the invention may more readily be understood, certain terms are defined:

The term "attach" or "attaches" as used herein refers to cells adhered directly to the three-dimensional scaffold or to cells that are themselves attached to other cells.

The terms "biocompatible matrix," "biocompatible substrate," "polymer scaffold," as used herein refer to a material that is suitable for implantation into a subject onto which a cell population can be deposited. A biocompatible substrate does not cause toxic or injurious effects once implanted in the subject. In one embodiment, the biocompatible substrate is a polymer with a surface that can be shaped into the desired organ that requires replacing. The polymer can also be shaped into a part of an organ that requires replacing. In another embodiment, the biocompatible substrate can be a decellularized structure. In another embodiment the biocompatible matrix is a three-dimensional scaffold comprising the infra-structure of a biocompatable matrix, e.g., polyglycolic acid, or the infra-structure left after decellularizing an organ by removing all cellular material. This complex, three-dimensional scaffold provides the supportive framework that allows cells to attach to it, and grow on it. Cultured populations of cells can then be grown on the three-dimensional scaffold, which provides the exact interstitial distances required for cell-cell interaction. This provides a reconstructed organ that resembles the native in vivo organ. This three-dimensional scaffold is perfused with at least one population of cultured female reproductive tract cells which grow and develop to provide female reproductive tract tissue layers. In another embodiment, the biocompatible matrix is biodegradable. Nonlimiting examples of biocompatible polymeric matrixes can be formed from materials selected from the group consisting of, but are not limited to, cellulose ether, cellulose, cellulosic ester, fluorinated polyethylene, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyglycolic acid, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, and copolymers or physical blends thereof. The polymeric matrix can be coated with a biocompatible and biodegradable shaped setting material. In one embodiment, the shape settling material can be a liquid copolymer. In another embodiment, the co-polymer is poly-DL-lactide-co-glycolide.

The term "decellularized structure" as used herein refers to a three-dimensional biological arrangement, (e.g., an organ, or part of an organ), produced by a process in which the entire cellular and tissue content is removed, leaving behind a complex infrastructure. The specialized tissue structures of an organ is the parenchyma which provides the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The term "decellularized structure" is intended to include whole organs from which the cellular and tissue material is removed. The term "decellularized structure" is also intended to include parts of an organ structure from which cellular and tissue material has been removed. The decellularized structure provides a biocompatible substrate onto which different cell populations can be infused. Decellularized structures can be rigid, or semi-rigid, having an ability to alter their shapes. For example, a decellularized uterus is capable of distending, but returns back to its original shape following giving birth. Examples of decellularized structures include, but are not limited to, decellularized uterus, vagina, cervix, ovary, and fallopian tube(s).

The terms "female reproductive organ" and "female reproductive tissue" as used herein are intended to include all organs or tissues associated with reproduction. These include, but are not limited to, vagina, uterus, ovary, fallopian tube, and cervix.

The terms "female reproductive cell population" and "female reproductive cells" as used interchangeably herein refer to cells derived from any region of the female reproductive system. The female reproductive system comprises organs which enable a female to produce eggs (ova), to have sexual intercourse, to nourish and house the fertilized ovum until it is fully developed, and to give birth. Female reproductive cell populations can be derived from organs such as, the vagina, cervix, uterus, fallopian tubes, and ovaries. The term is used to refer a mixture of cells that includes all cells from the female reproductive system. The term is also used to refer to an isolated sub-population of cells from a region of the female reproductive system, e.g., a single population of only vaginal cells, epithelial cells, endothelial cells. The isolated sub-population of cells can be derived from any region of the organ, e.g., the endometrium, myometrium, and perimetrium (See *Gray's Anatomy: The Anatomical Basis of Medicine and Surgery* 38$^{th}$ ed. Churchill Livingstone Eds. H. Gray, L. H. Bannister, M. Berry, P. L. Williams 1996). In one embodiment, the isolated sub-population is a homogeneous sub-population of cells. In one embodiment, female reproductive cell population refers to a cell population that is substantially vaginal, cervical, uterine, ovarian, or fallopian tube epithelial cells. In another embodiment, female reproductive cell population refers to a cell population that is substantially smooth muscle cells, e.g., myometrium. Cells from the female reproductive system can be derived by taking a biopsy from the subject. Cells from the female reproductive system can be derived from stem cells, embryonic stem cells, pediatric stem cells, fetal stem cells, adult stem cells, native cells, nuclear transfer, and parathenogenesis. Cell sorting techniques can be used to isolate healthy cells from diseased cells. Cell sorting techniques, e.g., FACS can also be used to isolated sub-populations of cells.

The term "vaginal epithelial cell population" or "vaginal epithelial cells" as used herein refer to cells derived from the vagina or cells native to the female vagina. Vaginal epithelial cells are intended to include endometrial cells. Vaginal epithelial cells comprise stratified squamous cells.

The terms "uterine epithelial cell population" and "uterine epithelial cells" as used herein refer to cells derived the female uterus or cells native to the female uterus including all cells in the cervix. Uterine epithelial cells are intended to include endometrial cells. Uterine epithelial cells comprise simple columnar cells that can be both ciliated and non-cilated columnar cells.

The terms "cervical epithelial cell population" and "cervical epithelial cells" as used herein refer to cells derived from the female cervix or cells native to the lower part of the female uterus. Cervical epithelial cells are intended to include endometrial cells. Cervical epithelial cells comprise columnar cells and squamous epithelial cells. The cervical epithelium cells comprise both ciliated and non-cilated columnar cells.

The terms "fallopian tube epithelial cell population" and "fallopian tube epithelial cells" as used herein refer to cells derived from the female fallopian tube or cells native to the female fallopian tube. Fallopian tube epithelial cells are intended to include endometrial cells. Fallopian tube epithelial cells comprise columnar cells that can be both ciliated and non-cilated columnar cells.

The term "substantially" as used herein in the context of cell population homogeneity refers to greater than 50% of the cells being from the same cell population, e.g., vaginal epithelial cells. Preferably, 70% of the cells are from the same cell population. More preferably, 85% of the cells are from the same cell population, even more preferably greater than 95%, 96%, 97%, 98% and 99% of the cells are from the same cell population.

The term "polylayer" as used herein refers to an arrangement comprising multiple layers of a homogenous cultured cell population layered over each other. The process of producing a "polylayer" involves depositing one layer of a cell population on a surface, e.g., a biocompatible substrate. The deposited cells are cultured in growth medium until they develop and proliferate to produce a first monolayer comprising cells with a desired phenotype and morphology. Once the first monolayer has attained a desired cell density, a second layer of the same cell population is depositing on the first monolayer. The second layer of deposited cells are cultured in growth medium which supplies nutrients to both the second cell layer and the first monolayer, until the cells in the second layer develop and proliferate to a desired cell density to produce a bilayer having cells with a desired phenotype and morphology. A third layer of same cell population is deposited on the bilayer, and the cells are cultured in growth medium which supplies nutrients to the bilayer and the cells of the third layer, until the cells of the third layer develop and proliferate to a desired density to produce a trilayer with a desired phenotype and morphology. The process is repeated until a polylayer comprising many layers of a homogenous cell population is produced. The characteristics of the polylayer is such that it closely resemble the morphology and functional characteristics of the equivalent parenchyma tissue of an in vivo organ. For example, a polylayer comprising a smooth muscle cell population may have functional characteristics of the smooth muscle tissue of a vagina or uterus, i.e., the myometrium.

The term "coupled" as used herein refers to the mutual intimate interactions between two different cell populations in contact with each other. These mutual interaction involve cell-cell interaction, growth, development, and proliferation. The cellular behavior responsible for the development, repair and maintenance of tissues is regulated, largely, by interactions between cells and components of their microenvironment. These interactions are mediated by cell surface molecules that bind, growth factors, enzymes, and other molecules that induce responses which result in changes of cellular phenotype. These interactions also result in the generation of new cells, which may be capable of generating cellular material with unique functional properties that is different from the functional properties of the each of the different cell populations.

The term "chimeric interface" as used herein refers to the boundary formed between two different cell populations.

The term "interstitial biomaterial" as used herein refers to the formation of cellular material at the chimeric interface where two different cell populations are in mutual contact with each other. The term "interstitial biomaterial" in its broadest concept is intended to include the formation of any new cellular material formed when two or more different cell populations are in contact with each other. The new cellular material resembles the functional equivalent cellular material produced in normal in vivo cellular development of the organ. For example, in the reconstruction of an artificial vagina, fallopian tube, or uterus, the two different cell populations in mutual contact with each other are the smooth muscle cell population, e.g. myometrium, and the epithelial cell population. The "interstitial biomaterial" produced at the interface of these two populations would therefore resemble that of the submucosa. In one embodiment, the biocompatible matrix degrades to form the submucosa.

The term "functional equivalent" as used herein refers to a structure, e.g., an artificial organ produced by the method of the invention that behaves in the same, or similar manner as a natural organ, for example, the artificial vagina has the same functional characteristics as an in vivo vagina.

The term "compound that modulates" is used herein and refers to a compound that causes a change cell activity. This change can be toxic, e.g., induce premature contractions resulting in abortion, or beneficial, e.g., enhance embryo implantation. The change can alter cell function, e.g. induce contraction, proliferation, apoptosis. The. modulator can also increase, decrease, elevate, or depress processes or signal transduction cascades involving a target gene or a target protein which leads to a change in cell activity.

The term "subject" as used herein refers to any living organism capable of eliciting an immune response. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, are intended to be covered.

The present invention provides compositions and methods for reconstructing artificial female reproductive organs. Construction of artificial female reproductive organs comprises perfusing at least one population of cultured female reproductive cells into a biocampatible matrix, such that cultured female reproductive cells attach to biocompatible matrix and form at least one female reproductive tissue layer. Additional populations of cultured female reproductive cells can be attached to the biocompatible matrix and cultured to produce an artificial female organ or tissue structure.

I. Anatomy a. Vagina

The vagina is a muscular tube, lined with stratified squamous epithelium that is histologically similar to the mucosa of the cervix and vulva, that joins the cervix (the lower part of uterus, or womb) to the outside of the body. The vagina, or birth canal, does not contain glands or hair follicles, but individual cells, crypts, produce mucus. The mucus helps keep bacteria out of the uterus and also helps sperm to enter the uterus when the egg is ready to be fertilized. The superficial layer is not keratinized. The vagina of the child and that of the postmenopausal woman are similar in that the epithelial layer is thin, easily traumatized, and subject to a variety of infections. The normal adult vagina contains diphtheroides, Doderlein *bacilli*, and anaerobic *streptococci*. This flora converts glycogen of vaginal cells to lactic acid, which maintains the vagina with an acid pH and enhances normal secretions. During menstrual life, the vagina has transverse folds called rugae. After menopause, in the absence of estrogen, the vaginal walls become thin and atrophic, reflecting the lack of estrogen, as seen in the childhood years. The adult vagina measures 12 to 13 cm in depth.

The vaginal epithelium is hormone-responsive. Estrogens stimulate the proliferation and maturation of the epithelium with accumulation of glycogen in the cells. The presence of glycogen in the epithelium forms the basis of the Schiller Test. The epithelium is supplied with Lugol's solution (strong iodine). The glycogen combines with the iodine to produce a deep mahogany-brown color. Nonstaining (positive test) implies an abnormal epithelium such as scar tissue, columnar epithelium (adenosis), and neoplasia or precursor lesion. Progestogens, however, inhibit maturation of the epithelium.

The vagina is a partially collapsed tubular structure that extends from the vestibule of the vulva to the uterus. The anterior and posterior walls are in contact with each other except at the apex where the vagina surrounds the ectocervix and vault-like recesses, called the fornices, separate the vagina and cervix. The posterior fornix is deeper than the anterior. The base of the bladder and urethra are anterior to the vagina while the rectum is posterior to it. The vagina derives its blood supply from two major sources: the uterine and pudendal arteries. The internal pudendal artery supplies the vagina from inferior to superior. The vaginal artery, often a branch from the uterine artery, and the uterine artery itself supply the superior position of the vagina.

The myometrium of the adult woman normally undergoes spontaneous rhythmic contractions. The uteri of castrates lose this rhythmic contractibility. Hypertrophy of myometrium occurs when higher levels of estrogen are present, and uterine atrophy occurs after menopause. The endometrium generally reflects the levels of estrogen and progesterone. Estrogen causes proliferation of the endometrium and its vascular channels. Progesterone transforms proliferative into secretory endometrium, with glandular and stromal features that promote possible implantation. Endometrial biopsy may allow precise interpretation of ovarian hormonal production.

In one embodiment, the methods and compositions of the present invention can be employed to construct an artificial vagina as demonstrated in Examples 1-3. The artificial vagina is a functional equivalent of a normal vagina. The artificial vagina comprises the cell structure, function, and physiology of a normal vagina. The artificial vagina can be produced by providing a biocompatible matrix, perfusing a first cell population on or in the biocompatible matrix, the first cell population being substantially a vaginal epithelial cell population, perfusing a second cell population of a different cell type than the first cell population, e.g. smooth muscle cells, on or in the biocompatible matrix; and culturing the cell populations in the biocompatible matrix.

b. Cervix

The cervix is the inferior portion of the uterus. The cervix is a fibromuscular organ covered with stratified squamous epithelium. The portio vaginalis of the cervix arises in the vaginal fornices and ends at the external cervical os at the entrance of the endocervical canal. This squamocolumnar junction is the most common site of origin of squamous cell carcinoma. The endocervical canal is lined by columnar epithelium, and racemose glands, lined with similar epithelium, are found in the fibromuscular stroma. Such glands, if obstructed, may form nabothian cysts on the cervical surface. The nulliparous cervical os is round, but parturition changes this to a horizontally flattened orifice. The cervix is the second most common site of genital malignancy in women.

In one embodiment, the methods and compositions of the present invention can be employed to construct an artificial cervix. The artificial cervix is a functional equivalent of a normal cervix. The artificial cervix comprises the cell structure, function, and physiology of a normal cervix. The artificial cervix can be produced by providing a biocompatible matrix, perfusing a first cell population on or in the biocompatible matrix, the first cell population being substantially a cervical epithelial cell population, perfusing a second cell population of a different cell type than the first cell population, e.g. smooth muscle cells, on or in the biocompatible matrix; and culturing the cell populations in the biocompatible matrix.

c. Fallopian Tubes

The fallopian tubes arise from the superior portion of the lateral borders of the uterus, superior to the attachment of the round ligaments, and are patent. The distal ends, the fimbriae, open into the abdominal cavity, and the proximal ends open into the uterine cavity. The tubes are lined by a single layer of low columnar epithelium, some ciliated, arranged in a branching or frond pattern. This structure is divided into interstitial, isthmic, ampullar, and fimbriated portions. The wall is thin with two muscular layers and an outer layer of peritoneum within the upper borders of the broad ligament.

The fallopian tube epithelium also reflects ovarian hormonal changes through cyclical modification, maturation, and regression changes. The tubal musculature possesses an intrinsic peristaltic action believed to aid tubal transport. The action of cilia of certain tubal cells may also be involved in transport. Estrogen appears to influence these activities.

The fallopian tubes, are attached to the upper part of the uterus on either side and are about 10 cm long. The fallopian tubes are narrow, muscular tubes that serve as tunnels for the ova to travel from the ovaries to the uterus. Each month, at the time of ovulation, a mature egg is released by an ovary. The fimbria, a bordering fringe at the end of the fallopian tubes, draws the egg into the fallopian tube. Each fallopian tube is lined by millions of tiny hairs called cilia that beat rhythmically to propel the egg forward. Conception, the fertilization of an egg by a sperm, normally occurs in the fallopian tubes. The fertilized egg then moves to the uterus, where it implants to the uterine wall. The fallopian tube also performs other functions, including nourishing the egg and the early embryo in its cavity.

In one embodiment, the methods and compositions of the present invention can be employed to construct an artificial fallopian tube as demonstrated in Example 4. The artificial fallopian tube is a functional equivalent of a normal fallopian tube. The artificial fallopian tube comprises the cell structure, function, and physiology of a normal fallopian tube. The artificial fallopian tube can be produced by providing a biocompatible matrix, perfusing a first cell population on or in the biocompatible matrix, the first cell population being substantially a fallopian tube cell population, perfusing a second cell population of a different cell type than the first cell population, e.g. smooth muscle cells, on or in the biocompatible matrix; and culturing the cell populations in the biocompatible matrix.

d. Ovaries

The normal ovary is a white, almond-shaped structure measuring 2×3×3 cm and is located on the posterior surface of the broad ligament and inferior to the fallopian tube. The ovaries produce the ova (egg cells), the female cells of reproduction, and produce hormones. The nerves, lymphatics, and blood vessels enter the ovary at the point of attachment to the broad ligament, the hilus. Lateral support of the ovary is provided by the infundibulopelvic ligament, which extends to the pelvic side wall, and the medial support is to the uterus by the utero-ovarian ligament. The ovary has a cortex and a medulla. Germinal epithelium, a single layer of cuboidal cells, covers condensed fibrous tissue, the tunica albuginea. Follicles originate within the ovarian cortex and are composed of the basic embryonic complement; no new follicles are formed after birth. The medullary portion of the ovary is occupied by blood vessels, lymphatics, nerves, and connective tissue and contains remnants of wolffian body precursors. The ovary is an endocrine and a generative organ. Parafollicular granulosa cells produce estrogen and, after ovulation and corpus luteum formation, progestins. Androgens are produced by stromal cells, particularly in the hilus.

In one embodiment, the methods and compositions of the present invention can be employed to construct an artificial ovary. The artificial ovary is a functional equivalent of a normal ovary. The artificial ovary comprises the cell structure, function, and physiology of a normal ovary.

e. Uterus

The uterus is a muscular organ in the female reproductive tract lined by glandular mucosa, which has a specialized vascularization. This hollow, pear-shaped organ is situated in the pelvic cavity interposed between the bladder and the rectum. In nonpregnant women the uterus measures approximately 8 cm in length and weighs 30 to 100 g. The fallopian tubes and the cervical canal communicate with the uterine cavity, which is lined by the endometrium. The expanded upper portion is called the body or corpus. The corpus is highly muscular so that it can enlarge to hold a developing baby. The area rostral to the point at which both oviducts join the uterus is often referred as the fundus. The uterine fundus is covered by peritoneum except in the lower anterior portion, where the bladder is contiguous with the lower uterine segment and the peritoneum is reflected, and laterally where the folds of the broad ligament are attached. The constricted portion below the fundus is called the isthmus, below which there is a cylindrical portion called the cervix. The layers of this organ from internal to external are mucosa (endometrium), muscularis (myometrium), and serosa (perimetrium). Fluctuations in the levels of serum estradiol and progesterone cause all three layers to go through sequential structural cyclic changes. The uterus is supported by condensations of endopelvic fascia and fibromuscular tissue laterally at the base of the broad ligaments. The round ligaments provide support laterally, and the uterovesical fold provides support anteriorly.

The endometrium is approximately 5 mm thick but varies throughout the hormonal cycle. This layer is lines by a secretory simple columnar epithelium invaginated to form tubular uterine glands. Some ciliated columnar cells can also be found as part of the epithelium. The endometrium is composed of an upper stratum functionalis, which sheds during each menstration. Coiled or spiral arteries that nurture a large capillary bed in the superficial endometrium supply vascularization of both strata. Although glandular and luminal epithelia are continuous with each other and appear to be morphologically similar by light and electron microscopy (Davies et al. *Am. J. Anat.* 137 (4):423-445 (1973); Davies et al. *Am. J. Anat.* 142(3): 335-365 (1975)), they respond differently to hormonal stimulus.

The uterine epithelium is composed of quiescent and proliferating subpopulations, which show differential proliferative responses to estrogens and progesterones (Conti et al. *Endocinology* 114(2): 345-351 (1984)). Administration of estrogen results in the recruitment of quiescent glandular cells into the cell cycle and decreases the rate of luminal cell loss. Progesterone induces acceleration in the rate of proliferation by shortening the cell cycle length in the glands and lumen (Nawaz et al. *Am. J. Pathol.* 127(1): 51-59 (1987)).

The endometrial stroma resembles mesenchyme, containing stellate cells with large ovoid nuclei. Owing to decidual transformation, stromal cells are believed to play a role in implantation and in the maintenance of pregnancy through nutrition of the blastocyst, endocrine secretion (prolactin), and protection of the embryo. The myometrium of the uterus is composed of four layers. The layers are not sharply demarcated because of complex interconnecting bundles, which are interspersed with considerable connective tissue. Four layer are easily recognizable: The stratum submucosum contains a thin layer beneath the submucosa with longitudinal fibers. The stratum vasculare, contains many large blood vessels that give it a spongy appearance, the fibers are circular and oblique. The stratum supravasculare has fibers that are mainly circular and longitudinal. The stratum subserosum consists of a thin longitudinal muscle layer. The peritoneum consists of a single layer of flattened cells, which surround the oviduct and uterus. This thin layer also functions as a sheath over the nerves and vessels. The portion of the peritoneum, which surrounds the uterus and extends to the pelvic walls laterally, is called the perimetrium (Baez and Atala, "Uterus" In: *Methods of Tissue Engineering.* Academic Press 2002 (1189-1194).

The arterial blood supply to vagina, uterus, fallopian tubes, and ovaries is through four paired arteries: the ovarian arteries, the uterine arteries, the vaginal arteries, and the internal pudendal arteries. The uterus, cervix, and upper vagina are behind the bladder, which is separated from the uterus by the vesicouterine fold. Below this peritoneal fold, the bladder is connected to the cervix and upper vagina by areolar tissue.

In one embodiment, the methods and compositions of the present invention can be employed to construct an artificial as demonstrated in Examples 5 and 6. The artificial uterus is a functional equivalent of a normal uterus. The artificial uterus comprises the cell structure, function, and physiology of a normal uterus. The artificial uterus can be produced by providing a biocompatible matrix, perfusing a first cell population on or in the biocompatible matrix, the first cell population being substantially a uterine epithelial cell population, perfusing a second cell population of a different cell type than the first cell population, e.g. smooth muscle cells, on or in the biocompatible matrix; and culturing the cell populations in the biocompatible matrix.

f. Function of the Female Reproductive System

Females of reproductive age experience cycles of hormonal activity that repeat at about one-month intervals. With every cycle, a woman's body prepares for a potential pregnancy. The term menstruation refers to the periodic shedding of the uterine lining. The average menstrual cycle takes about 28 days and occurs in phases: the follicular phase, the ovulatory phase (ovulation) and the luteal phase. There are four major hormones, chemicals that stimulate or regulate the activity of cells or organs, involved in the menstrual cycle: follicle-stimulating hormone (FSH), luteinizing hormone (LH), estrogen and progesterone.

The first phase, the follicular phase, begins with the first day of the menstrual cycle, the day the menstrual period begins. During this phase, follicle stimulating hormone (FSH) and luteinizing hormone (LH) are released by the pituitary gland located at the base of the brain. These hormones travel in the blood to the ovaries. There, the hormones stimulate the growth of about 15 to 20 eggs, each in its own follicle. A follicle is a small, fluid-filled cyst that holds the egg and the supporting cells responsible for the growth and nurturing of the egg. FSH and LH also cause the follicle to increase estrogen production.

As estrogen levels rise throughout the natural menstrual cycle, the pituitary gland produces less FSH. The balance of hormones allows the body to limit the number of follicles that complete maturation. As the follicular phase progresses, one follicle in one ovary becomes dominant and continues to mature. This dominant follicle suppresses all of the other follicles in the group, which stop growing and degenerate. The developing follicle produces its own hormones, including estrogen.

The second phase, the ovulatory phase, or ovulation, is the midpoint of the menstrual cycle, generally about two weeks before a woman's next menstrual period begins. During this phase, the rise in estrogen triggers a surge of LH from the pituitary gland. This causes the dominant follicle to release its egg from the ovary. As the egg is released, which is called ovulation, it is captured by finger-like projections on the end of the fallopian tubes (fimbriae). The fimbriae sweep the egg into the tube. Also during this phase, there is an increase in the woman's cervical mucus, which prepares to receive and nourish the man's sperm (male reproductive cells). The mucus also helps move the sperm through the cervical canal.

The third phase, the luteal phase begins right after ovulation. Once it releases its egg, the empty follicle develops into a new structure called the corpus luteum (hence the luteal phase). The corpus luteum secretes estrogen and progesterone. Progesterone prepares the uterus with the rich lining needed for the fertilized egg to implant. If the egg has been fertilized by the man's sperm, the fertilized egg (embryo) will travel through the fallopian tube to implant in the uterus, and pregnancy takes place. If the egg is not fertilized, it passes through the uterus. Not needed to support a pregnancy, the lining of the uterus breaks down and sheds, and the next menstrual period begins.

II. Biocompatible Substrates

In one aspect of the invention, the artificial female organ is with the aid of a support structure such as a polymeric structure, biocompatible matrix, or a decellularized organ.

a. Polymeric Structures

A biocompatible substrate refers to materials which do not have toxic or injurious effects on biological functions. Biodegradable refers to material that can be absorbed or degraded in a patient's body. Examples of biodegradable materials include, for example, absorbable sutures. Representative materials for forming the biodegradable structure include natural or synthetic polymers, such as, for example, collagen, poly(alpha esters) such as poly(lactate acid), poly(glycolic acid) (PGA), polyorthoesters and polyanhydrides and their copolymers, which degraded by hydrolysis at a controlled rate and are reabsorbed. These materials provide the maximum control of degradability, manageability, size and configuration. Preferred biodegradable polymer material include polyglycolic acid and polygalactin, developed as absorbable synthetic suture material. Polyglycolic acid and polygalactin fibers may be used as supplied by the manufacturer. Other biodegradable materials include cellulose ether, cellulose, cellulosic ester, fluorinated polyethylene, phenolic polymer, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

In some embodiments, attachment of the cells to the polymer is enhanced by coating the polymers with compounds such as basement membrane components, agar, agarose; gelatin, gum arabic, collagens, such as collagen types I, II, III, IV, and V, fibronectin, laminin, glycosaminoglycans, mixtures thereof, and other hydrophilic and peptide attachment materials having properties similar to biological matrix molecules known to those skilled in the art of cell culture. All polymers must meet the mechanical and biochemical parameters necessary to provide adequate support for the cells with subsequent growth and proliferation. Factors, including nutrients, growth factors, inducers of differentiation or dedifferentiation, products of secretion, immunomodulators, inhibitors of inflammation, regression factors, biologically active compounds which enhance or allow ingrowth of the lymphatic network or nerve fibers, and drugs, can be incorporated into the matrix or provided in conjunction with the matrix. Similarly, polymers containing peptides such as the attachment peptide RGD (Arg-Gly-Asp) can be synthesized for use in forming matrices.

In one embodiment, the biocompatible polymer is polyglactin and polyglycolic acid. Polyglactin was developed as absorbable synthetic suture material, a 90:10 copolymer of glycolide and lactide, manufactured as Vicryl braided absorbable sutures (Ethicon Co., Somerville, N.J.) (Craig P. H., Williams J. A., Davis K. W., et al.: A Biological Comparison of Polyglactin 910 and Polyglycolic Acid Synthetic Absorbable Sutures. Surg. 141; 1010, (1975)). Polyglactin and polyglycolic acid fibers can be used as supplied by the manufacturer. The biocompatible polymer may be shaped using methods such as, for example, solvent casting, compression molding, suturing, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the matrix; next a solvent is used to dissolve away one of the components, resulting in pore formation. (See Mikos, U.S. Pat. No. 5,514,378, hereby incorporated by reference). In nucleation, thin films in the shape of a matrix are exposed to radioactive fission products that create tracks of radiation damaged material. In one embodiment, the biocompatible matrix can be biodegradable polymer meshes composed of fibers.

The polycarbonate sheets can be etched with acid or base, turning the tracks of radiation-damaged material into pores. Finally, a laser may be used to shape and burn individual holes through many materials to form a matrix structure with uniform pore sizes. Coating refers to coating or permeating a polymeric structure with a material such as, for example, liquefied copolymers (poly-D,L-lactide co-glycolide (PLGA, 50:50) 80 mg/ml methylene chloride or in chloroform (5% w/v)) to alter its mechanical properties. Coating may be performed in one layer, or multiple layers until the desired mechanical properties are achieved. These shaping techniques may be employed in combination, for example, a polymeric matrix may be weaved, compression molded and glued together.

Furthermore different polymeric materials shaped by different processes may be joined together to form a composite shape. The composite shape may be a laminar structure. For example, a polymeric matrix may be attached to one or more polymeric matrixes of the same or different composition to form a multilayer prosthetic vaginal structure. The attachment may be performed by any suitable means such as gluing with a liquid polymer, stapling, suturing, or a combination of these methods. In addition, the polymeric matrix may be formed as a solid block and shaped by laser or other standard machining techniques to its desired final form. Laser shaping refers to the process of removing materials using a laser.

The polymers can be characterized with respect to mechanical properties such as tensile strength and stress.

In a preferred embodiment, polyglycolic acid (PGA) is used as a biomaterial. PGA has been widely used in tissue engineering. PGA scaffolds can be easily manipulated into various three dimensional structures, and offer an excellent means of support and transportation for cells (Christenson L, Mikos A G, Gibbons D F, et al: Biomaterials for tissue engineering: summary. *Tissue Eng.* 3 (1): 71-73; discussion 73-76, 1997). As shown in Examples 2 and 3, the vaginal epithelial and smooth muscle cells were successfully cocultured on PGA constructs. Examples 5 and 6 illustrate that PGA can be used to create an artificial uterus.

Biocompatible substrates can be treated with factors, such as angiogenesis factors, cytokines, extracellular matrix components, and other bioactive materials or drugs, prior to implantation, before or after the biocompatible substrate is coated with cultured cells, e.g., to promote the formation of new tissue after implantation and to promote graft healing. Factors including drugs, can be incorporated into the biocompatible substrate or be provided in conjunction with the biocompatible substrate. Growth factors and other additives (e. g., epidermal growth factor (EGF), vascular endothelial growth factor (VEGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the polymeric matrix, if added cells are employed. Such additives are preferably provided in an amount sufficient to promote the formation of the new female organ, such as the formation of novel vaginal tissue. Other useful additives include antibacterial and antifungal agents to promote healing by suppression of infections.

One preferred supporting matrix is composed of crossing filaments which can allow cell survival by diffusion of nutrients across short distances once the cell support matrix is implanted.

The biocompatible matrix can be fabricated to have a controlled pore structure that allows nutrients from the culture medium to reach the deposited cell population, but prevent cultured cells from migrating through the pores. In vitro cell attachment and cell viability can be assessed using scanning electron microscopy, histology and quantitative assessment with radioisotopes.

The biocompatible matrix can be shaped into any number of desirable configurations to satisfy any number of overall system, geometry or space restrictions. For example, in using a polymeric substrate for female reproductive organ construction, the substrate may be shaped to conform to the dimensions and shapes of the whole, or a part of a the organ, e.g., a vagina, or uterus. The bibcompatible matrix can be shaped to different sizes to conform to the vaginas, or uteruses of different sized patients. The polymeric substrate may also be shaped to facilitate special needs of a patient, for example, a disabled patient, who may have a different abdominal cavity space may require a vagina, or uterus reconstructed to adapt to fit the space.

In other embodiments, the biocompatible matrix is used for the treatment of laminar structures in the body such as fallopian tubes. In those applications the polymeric substrate can be shaped as a hollow tube.

b. Decellularized Structures

Biostructures, e.g., whole organs, or parts of organs can be decellularized by removing the entire cellular and tissue content from the organ. In one embodiment, decellularized female reproductive organs or tissue, such as vaginal, uterus, fallopian tubes, and cervix, can be used in the present invention. The decellularization process comprises a series of sequential extractions. One key feature of this extraction process is that harsh extraction that may disturb or destroy the complex infrastructure of the biostructure, be avoided. The first step involves removal of cellular debris and solubilization of the cell membrane. This is followed by solubilization of the nuclear cytoplasmic components an the nuclear components.

Preferably, the biostructure, e.g., an organ, is decellularized by removing the cell membrane and cellular debris surrounding the organ using gentle mechanical disruption methods. The gentle mechanical disruption methods must be sufficient to disrupt the cellular membrane. However, the process of decellularization should avoid damage or disturbance of the biostructure's complex infrastructure. Gentle mechanical disruption methods include scraping the surface of the organ or tissue, agitating the organ or tissue, or stirring the organ or tissue in a suitable volume of fluid, e.g., distilled water. In one preferred embodiment, the gentle mechanical disruption method includes stirring the organ or tissue in a suitable volume of distilled water until the cell membrane is disrupted and the cellular debris has been removed from the organ. In another embodiment, the organ or tissue is exposed to hypotonic conditions, such that blood cells are lysed while retaining the cellular matrix.

After the cell membrane has been removed, the nuclear and cytoplasmic components of the biostructure are removed. This can be performed by solubilizing the cellular and nuclear components without disrupting the infrastructure. To solubilize the nuclear components, non-ionic detergents or surfactants may be used. Examples of non-ionic detergents or surfactants include, but are not limited to, the Triton series, available from Rohm and Haas of Philadelphia, Pa., which includes Triton X-100, Triton N-101, Triton X-114, Triton X-405, Triton X-705, and Triton DF-16, available commercially from many vendors; the Tween series, such as monolaurate (Tween 20), monopalmitate (Tween 40), monooleate (Tween 80), and polyoxethylene-23-lauryl ether (Brij. 35), polyoxyethylene ether W-1 (Polyox), and the like, sodium cholate, deoxycholates, CHAPS, saponin, n-Decyl beta-D-glucopuranoside, n-heptyl beta-D glucopyranoside, n-Octyl alpha-D-glucopyranoside and Nonidet P-40.

One skilled in the art will appreciate that a description of compounds belonging to the foregoing classifications, and vendors may be commercially obtained and may be found in "Chemical Classification, Emulsifiers and Detergents", McCutcheon's, Emulsifiers and Detergents, 1986, North American and International Editions, McCutcheon Division, MC Publishing Co., Glen Rock, N.J., U.S.A. and Judith Neugebauer, A Guide to the Properties and Uses of Detergents in Biology and Biochemistry, Calbiochem. R., Hoechst Celanese Corp., 1987. In one preferred embodiment, the non-ionic surfactant is the Triton. series, preferably, Triton X-100.

The concentration of the non-ionic detergent may be altered depending on the type of biostructure being decellularized. For example, for delicate tissues, e.g., blood vessels, the concentration of the detergent should be decreased. Preferred concentrations ranges non-ionic detergent can be from about 0.001 to about 2.0% (w/v). More preferably, about 0.05 to about 1.0% (w/v). Even more preferably, about, 0.1% (w/v) to about 0.8% (w/v). Preferred concentrations of these range from about 0.001 to about 0.2% (w/v), with about 0.05 to about 0.1% (w/v) particular preferred.

The cytoskeletal component, comprising consisting of the dense cytoplasmic filament networks, intercellular complexes and apical microcellular structures, may be solubilized using alkaline solution, such as, ammonium hydroxide. Other alkaline solution consisting of ammonium salts or their derivatives may also be used to solubilize the cytoskeletal components. Examples of other suitable ammonium solutions include ammonium sulphate, ammonium acetate and ammonium hydroxide. In a preferred embodiment, ammonium hydroxide is used. In one embodiment, the mild base is a hydroxide or non-hydroxide base. Non-limiting examples of non-hydroxide bases include ammonium or sodium salts, or their derivatives, of acetate, benzoate, propionate, and phenoxide. Non-limiting examples of hydroxide bases include ammonium hydroxide, trimethylammonium hydroxide, triethanolammonium hydroxide, monoethanolammonium hydroxide, and benzylammonium hydroxide.

The concentration of the alkaline solutions, e.g., ammonium hydroxide, may be altered depending on the type of biostructure being decellularized. For example, for delicate tissues, e.g., fallopian tubes, the concentration of the detergent should be decreased. Preferred concentrations ranges can be from about 0.001 to about 2.0% (w/v). More preferably, about 0.005 to about 0.1% (w/v). Even more preferably, about, 0.01% (w/v) to about 0.08% (w/v).

The decelluarized organ may be dehydrated by any means known in the art, such as baking, freeze-drying, lyphylization. The decellularized organ can be mounted on an element during dehydration.

The decellularized, dehydrated structure may be stored at a suitable temperature until required for use. Prior to use, the decellularized structure can be equilibrated in suitable isotonic buffer or cell culture medium. Suitable buffers include, but are not limited to, phosphate buffered saline (PBS), saline, MOPS, HEPES, Hank's Balanced Salt Solution, and the like. Suitable cell culture medium includes, but is not limited to, RPMI 1640, Fisher's, Iscove's, McCoy's, Dulbecco's medium, and the like.

III. Culturing Cells

Tissue engineering may offer a solution for the challenging cases where a shortage of local tissue exists. The successful creation of prefabricated organs in the laboratory from autologously derived cells that are phenotypically normal can result in normal functional development. In Examples 2 and 3, the methods and compositions of the present invention were used to demonstrate that vaginal cells cultured in vitro can be used to create reconstituted, viable vaginal tissue in vivo.

The present invention describes compositions and methods for female organ reconstruction. Generally, the invention features multicellular organs comprising at least two different cell populations. The organ constructs comprise a first cultured population of cells derived from a first cell population, and a second cultured population of cells derived from a second cell population that is different from the first cell population, wherein the second cell population is coupled to the first by a chimeric interface to produce a construct that is the functional equivalent of a natural biological structure.

The invention also features methods for producing artificial female organs using a biocompatible substrate in the shape of an organ, by creating a first cultured population of cells derived from a first cell population on one area of the biocompatible substrate, the first cultured cell population is attached to the biocompatible substrate; creating a second cultured cell population of cells derived from a second cell population that is different from the first cell population, the second cell population is coupled to the first by a chimeric interface such that the construct provides the functional equivalent of a natural biological structure upon implantation, thereby producing an artificial female organ construct.

a. Cell Harvesting

The availability of an abundance of easily retrievable tissue sources is imperative for the success of any experimental design involving animal models and tissue engineering. The reconstructed artificial female reproductive organ can be allogenic, where the cell populations are derived from the subject's own tissue. For example, vaginal epithelial cells can be derived from the subject's vagina and cultured in vitro.

The reconstructed artificial female reproductive organ can also be xenogenic, where cell populations are derived from a mammalian species that are different from the subject. For example the different cells can be derived from organs of mammals such as monkeys, dogs, cats, mice, rats, cows, horses, pigs, goats and sheep. Such organs can be obtained by appropriate biopsy or upon autopsy. Cadaver organs may be used to provide a supply of endothelial cells and elements. The isolated cells are preferably autologous cells, obtained by biopsy from the subject. For example, a biopsy of skeletal muscle from the arm, forearm, or lower extremities, or smooth muscle from the area treated with local anaesthetic with a small amount of lidocaine injected subcutaneously, and expanded in culture. The biopsy can be obtained using a biopsy needle, a rapid action needle which makes the procedure quick and simple. The small biopsy core of either skeletal or smooth muscle can then be expanded and cultured as described in the Examples. Cells from relatives or other donors of the same species can also be used with appropriate immunosuppression.

Endometrial cells can be obtained from uterine biopsy or hysterectomy specimens. Biopsies should be transferred immediately to transport medium: DMEM/F-12 (Dulbecco's Modified Eagle's Medium with Ham's F-12 nutrient medium). Biopsies exceeding 2 cm in diameter will remain visible in this medium for up to 3 days at 4° C. In Example section, the New Zealand white rabbit is shown to be an excellent source of vaginal tissue that can be harvested through a simple, midline, transabdominal approach allowing for good exposure during the harvest of tissue. The rabbit's vagina has ample size and girth and allows for excellent tissue yield during each procedure. The harvested specimen is transported in sterile culture medium to the laboratory, where the process of separating the individual tissue layers begins.

b. Cell Isolation and Culture

Methods for the isolation and culture of cells are discussed by Freshney, Culture of Animal Cells. A Manual of Basic Technique, 2d Ed., A. R. Liss, Inc., New York, 1987, Ch. 9, pp. 107B126 and Fauza et al. (1998) *J. Ped. Surg.* 33, 7-12, incorporated herein by reference. Cells may be isolated using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, and dispase. Mechanical disruption can also be accomplished by a number of methods including, but not limited to, scraping the surface of the organ, the use of grinders, blenders, sieves, homogenizers, pressure cells, or insonators to name but a few. For a review of tissue disaggregation techniques, see Freshney, (1987), Culture of Animal Cells. A Manual of Basic Technique, 2d Ed., A. R. Liss, Inc., New York, Ch. 9, pp. 107-126.

Preferred cell types include, but are not limited to, uterine epithelial cells, myometrial cells, vaginal epithelial cells, cervical epithelial cells, fallopian tube epithelial cells, uterine epithelial cells, ovarian epithelial cells and smooth muscle cells. In a preferred embodiment human vaginal epithelial cells and smooth muscle cells are isolated. In other embodiment, human cervical epithelial cells and smooth muscle cells are isolated. In other embodiment, human fallopian tube epithelial cells and smooth muscle cells are isolated. In other embodiment, human ovarian epithelial cells and smooth muscle cells are isolated. In another preferred embodiment human uterine epithelial cells and myometrial cells are isolated.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting (see e.g. Freshney, (1987) Culture of Animal Cells. A Manual of Basic Techniques, 2d Ed., A. R. Liss, Inc., New York, Ch. 11 and 12, pp. 137B168). For example, endothelial cells may be enriched by fluorescence-activated cell sorting.

c. Cell Expansion

Isolated cells can be cultured in vitro to increase the number of cells available for infusion into the three-dimensional scaffold. The use of allogenic cells, and more preferably autologous cells, is preferred to prevent tissue rejection. However, if an immunological response does occur in the subject after implantation of the reconstructed artificial organ, the subject may be treated with immunosuppressive agents such as, cyclosporin or FK506, to reduce the likelihood of rejection. In certain embodiments, chimeric cells, or cells from a transgenic animal, can be perfused onto the three-dimensional scaffold.

Isolated cells may be transfected prior to coating with genetic material. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection could also be used for gene delivery. Vaginal epithelial cells could be transfected with specific genes prior to infusion into the three-dimensional scaffold. The artificial reconstructed organ could carry genetic information required for the long term survival of the host or the reconstructed artificial organ.

The female reproductive tract cells grown on the biocompatible matrix may be genetically engineered to produce gene products beneficial to transplantation, e.g., anti-inflammatory factors, e.g., anti-GM-CSF, anti-TNF, anti-IL-1, and anti-IL-2. Alternatively, the endothelial cells may be genetically engineered to "knock out" expression of native gene products that promote inflammation, e.g., GM-CSF, TNF, IL-1, IL-2, or "knock out" expression of MHC in order to lower the risk of rejection. In addition, the endothelial cells may be genetically engineered for use in gene therapy to adjust the level of gene activity in a patient to assist or improve the results of tissue transplantation.

Methods for genetically engineering cells with retroviral vectors, polyethylene glycol, or other methods known to those skilled in the art can be used. These include using expression vectors which transport and express nucleic acid molecules in the cells. (See Geoddel; Gene Expression Technology: Methods in Enzymology 185, Academic Press, San Diego, Calif. (1990).

Vector DNA is introduced into prokaryotic or eukaryotic cells via conventional transformation or transfection techniques. Suitable methods for transforming or transfecting host cells can be found in Sambrook et al. Molecular Cloning: *A Laboratory Manual,* 2nd Edition, Cold Spring Harbor Laboratory press (1989), and other laboratory textbooks.

The growth of cells in the three-dimensional scaffold may be enhanced by adding, or coating the three-dimensional scaffold with proteins (e.g., collagens, elastic fibers, reticular fibers) glycoproteins, glycosaminoglycans (e.g., heparan sulfate, chondroitin-4-sulfate, chondroitin-6-sulfate, dermatan sulfate, keratin sulfate, etc.), a cellular matrix, and/or other materials.

After perfusion or layering of the female reproductive tract cells, the three-dimensional scaffold should be incubated in an appropriate nutrient medium. Many commercially available media such as RPMI 1640, Fisher's, Iscove's, McCoy's, Dulbecco's medium, and the like, may be suitable for use. The culture medium should also be changed periodically to remove the used media, depopulate released cells, and add fresh media. It is important to grow the female reproductive tract cells to a stage where female reproductive tract tissue layer has developed.

Growth factors and regulatory factors can be added to the media to enhance, alter or modulate proliferation and cell maturation and differentiation in the cultures. The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include prostaglandins, interleukins, and naturally-occurring chalones.

Cells grown on the biocompatible matrix, in accordance with the present invention, grow in multiple layers, forming a cellular matrix that resembles physiologic conditions found in vivo. The three-dimensional scaffold with at least one layer of a female reproductive tissue layer may support the proliferation of different types of cells and the formation of a number of other different tissues. In one embodiment, one cell population can be an endothelial cell population. Angiogenesis is a process of new blood vessel development and plays a critical role in the female reproductive cycle e.g., ovulation, menstruation and placental development. The endothelial cell population can be used to stimulate vascularization.

When the artificial reconstructed female reproductive organ is to be used for transplantation or implantation in vivo, it may be preferable to obtain the female reproductive cells, e.g., vaginal epithelial cells and smooth muscle cells, from the individual who is to receive the transplant or implant. This approach might be especially advantageous where immunological rejection of the transplant and/or graft versus host disease is likely.

Once perfused onto the biocompatible matrix, the female reproductive cells will proliferate and develop on the matrix to form female reproductive tissue layer. During in vitro culturing, the female reproductive cells develop and differentiate to produce a female reproductive tissue layer that may be capable of supporting the growth of other cells and produce structures that have a morphology which resembles the analogous structure in vivo. The physiology of the produced female reproductive tissue resembles that of normal female reproductive tissue. For example, the artificial female organ is responsive to hormones.

At puberty, the hypothalamus increases the release of gonadotropin releasing hormone (GnRH). The anterior pituitary gland then produces gonadotropins, follicle stimulating hormone (FSH) and lutenizing hormone (LH), controlled by GnRH and by the ovarian hormones estrogen and progesterone. FSH stimulates the development of follicles. LH surge causes ovulation. These gonadotropins stimulate the production of the sex hormones, estrogens and progestins. The interaction of the gonodotropic hormones and the ovarian hormones control the reproductive cycle. The sudden increase of lutenizing hormone (LH) causes the mature follicle to release the egg. Following release of the ovum, the ruptured ovarian follicle develops into the corpus luteum, which then secretes estrogen and progesterone. These ovarian hormones are important for the maintenance of the endometrial lining of the uterus where the blastocyst implants itself. In one embodiment, the artificial female reproductive organ is an artificial uterus capable of responding to hormones. In another embodiment, the artificial uterus is capable of responding to and producing sex hormones, e.g. estrogen and progesterone. In another embodiment, the artificial uterus is capable of hormone regulated cyclic events, e.g., building and shedding the endometrial lining, in preparation of uterus to receive the fertilized embryo. In another embodiment, the artificial uterus is capable of blastocyst implantation and of supporting a growing fetus. The artificial uterus can be implanted into an autologous subject. For example, the cells can be cultured from the same subject into which the artificial female organ is implanted. In another embodiment, the artificial uterus can be used to support the growth of a fetus outside of a homologous subject. Thus, the artificial uterus can be used to support a growing fetus in vitro. Alternatively, the artificial uterus can be implanted into an heterologous subject.

In another embodiment, the artificial vagina is responsive to hormones and sensory stimulation similar to a normal vagina. The cells of the artificial vaginal are capable of producing producing mucus. The artificial vagina comprises vaginal epithelium that is hormone-responsive. Estrogen stimulates the proliferation and maturation of the vaginal epithelium while progestogens inhibit maturation of the epithelium. The artificial vagina is capable of contraction.

In another embodiment, the artificial fallopian tube resembles the physiology of a normal fallopian tube. The artificial fallopian tube is responsive to hormones and is capable of peristaltic action. The artificial fallopian tube is capable of transporting the ova from the ovaries to the uterus and can be the site of fertilization of the egg by sperm.

It is important to recreate, in culture, the cellular microenvironment found in vivo for the particular female reproductive organ being reconstructed. The extent to which the female reproductive cells are grown prior to use in vivo may vary depending on the type of female reproductive organ being reconstructed.

In one embodiment, the three-dimensional scaffold can be pre-treated with, for example, collagen, prior to perfusion of cultured female reproductive tract cells, e.g., vaginal epithelial cells, in order to enhance the attachment of female reproductive tract cells to the three-dimensional scaffold. In another embodiment, factors selected from the group consisting of nutrients, growth factors, cytokines, extracellular matrix components, inducers of differentiation, products of secretion, immunomodulators, biologically-active compounds which enhance or allow growth of the cellular network or nerve fibers can be added to the scaffold or female reproductive cells.

The cultured female reproductive tract cells can be perfused into the biocompatible matrix using needles placed in localized positions in the three-dimensional scaffold, or layered onto the scaffold. The female reproductive tract cells can be expanded by culturing them in vitro to the desired cell density prior to placing them into or onto the three-dimensional scaffold. Examples 2 and 3 demonstrate how the present invention can be used to create reconstituted vaginal tissue in vivo. Examples 5 and 6 demonstrate how the present invention can be used to create reconstituted uterine tissue in vivo. Cultured epithelial and smooth muscle cell types maintain normal phenotypic expression and were propagated into a large repository of cells adaptable for tissue replacement. The cell seeded polymer scaffolds were to form vascularized vaginal and uterine tissue that have similar phenotypic and functional properties to native vagina and uterus. The present invention can be used to achieve vascularized engineered vaginal, uterus, fallopian tube, and cervical tissues for clinical applications.

d. Tissue Processing and Cell Culturing

The tissues can be processed and cultured according to methods known in the art. In a preferred embodiment, several wash cycles with phosphate-buffered saline (PBS) containing ethylenediamenetetracetic acid (EDTA) are performed. The specimen can be placed into a clean reservoir of culture medium until the process of microdissection begins.

A variety of commercially manufactured culture media are available for epithelial and smooth muscle cell growth. In a preferred embodiment, Dulbecco's Modified Eagle's Medium supplemented with 10% fetal bovine serum (DMEM/FBS) is used for smooth muscle cells and vaginal epithelial cells (keratinocytes) are cultured in serum-free medium specifically for keritinocytes, supplemented with bovine pituitary extract and epidermal growth factor (K-SFM).

Several techniques can be used for achieving the separation and culture of epithelial cells, e.g., endometrial cells, including methods based on enzymatic digestion and mechanic dissociation (Watson et al. *J. Reprod. Fertil.* 101(2): 415-420 (1994); Akoum et al. *J. Reprod. Med.* 41(8): 551-561 (1996); Barberini et al. *Cell Tissue Res.* 190(2): 207-222 (1978); Bentin-Ley et al. *J. Reprod. Fertil.* 101(2): 327-332 (1994)). Homogenous cell populations can be created in which the cells are substantially a single cell population. In a preferred embodiment, epithelial and smooth muscle cells are grown separately, and isolation of the individual cell types involves one of two processes that consist of either an explant method or enzymatic digestion. Descriptions of these methods can be found in the following references which are herein incorporated by reference in their entirety: Williams et al. *Methods Mol. Biol.* 5: 139-149 (1989); Baez, C. E. and Atala, A. "Uterus" In: Methods of Tissue Engineering. Academic Press 1189-1194 (2002); De Filippo, R. E. and Atala, A. "Epithelial Cell Culture: Vaginal Cell Reconstruction." In: Methods of Tissue Engineering. Academic Press 273-275 (2002).

In one embodiment, the explant method is used to isolate cells. The explant method begins with careful microdissection with sterile instruments under loop magnification, separating the epithelial and seramuscular layers. In one embodiment, detubularizing the vagina into a flat segment is done to facilitate the dissection. Small portions of the tissue are individually placed onto culture dishes, where they dry and adhere to the surface. The pieces of tissue are incubated with the appropriate medium at 37° C. in air and 5% $CO_2$ undisturbed until a sufficient colony of progenitor cells develops from the tissue islets, which usually takes approximately 5-7 days. The explants can be removed by gentle suction and the cells maintained with scheduled replacement of the medium.

In another embodiment, the enzymatic digestion is used to isolate cells. The cultured female reproductive tract cells may be readily isolated by disaggregating an appropriate organ or tissue which is to serve as the source of the cells. This may be accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include, but are not limited to, trypsin, chymotrypsin, collagenase, elastase, and/or hyaluronidase, DNase, pronase, and dispase. Mechanical disruption can also be accomplished by a number of methods including, but not limited to, the use of grinders, blenders, sieves, homogenizers, pressure cells, or insonators to name but a few. (See e.g. Freshney, (1987) Culture of Animal Cells. A Manual of Basic Technique, 2d Ed., A. R. Liss, Inc., New York, Ch. 9, pp. 107B126.)

In one embodiment, a method of enzymatic digestion has been applied for the processing and culture of epithelial cells. The fastidious nature of epithelial cells sometimes makes growth to large quantities difficult. However, success in achieving ample colony sizes has been possible with enzymatic digestion. In a preferred embodiment, powder forms of collagenase type IV and dispase, a neutral protease, are combined and suspended with K-SFM. This collagenase-medium solution can then be filtered to ensure sterility. The vaginal, uterus, cervix, or fallopian tube specimen is cut into several large pieces, immersed into the enzymatic solution, and vigorously shaken. With gentle pipette suction, the cell-fluid suspension is transferred to another sterile tube and centrifuged at low revolutions. Finally, the supernatant is removed and the cell pellet resuspended in medium and distributed into culture dishes.

e. Cell Expansion

Known methods of cell expansion well known in the art can be employed. In one embodiment, passage of the cells is performed by first removing the culture medium and washing the cells with PBS-EDTA. The cells can be incubated with a trypsin-EDTA solution and monitored under the microscope until cell separation is observed. Gentle pipette suction can be used to remove the cell-tryspin solution into a sterile tube with serum-containing medium to inactivate the tryspin. The cells are centrifuged at low revolutions. The cell pellet is resuspended to a predetermined volume with fresh medium and portioned equally among several more culture dishes for expansion.

IV. Cell Characterization

After reducing the tissue to a suspension of individual cells, the suspension can be fractionated into subpopulations from which the female reproductive tract cells can be obtained. Homogenous cell populations can be obtained in which each cell population comprises substantially the same cells, e.g., a vaginal epithelial cell population. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. (See e.g. Freshney, (1987) Culture of Animal Cells. A Manual of Basic Techniques, 2d Ed., A. R. Liss, Inc., New York, Ch. 11 and 12, pp. 137B168.) For example, smooth muscle cells may be enriched by fluorescence-activated cell sorting, and epithelial cells may be reduced for smooth muscle cell collection.

Cells can be characterized though the use of specific differentiation markers. Endometrial epithelia markers include keratin intermediate filaments, intracytoplasmic glycogen, progesterone receptors, and estrogen receptors (Centola et al. *In Vitro* 20 (6): 451-4612 (1984); Cooke et al. *Proc. Natl. Acad. Sci. USA* 83(7): 2109-2113 (1986); Johnson et al. *Biol. Reprod.* 61(5): 1324-1330 (1999); Kirl et al. 14 (8): 651-662 (1978); Merviel et al. *Biol. Cell.* 53(3): 636-646 (1995); Osteen et al. *Fertil. Steril.* 52 (6): 965-972 (1989); Schatz et al. *Biol. Reprod.* 62(3): 691-697 (2000). Cytokeratin intermediate filaments (Bongo et al. *Hum. Reprod.* 3(6): 705-713 (1988); Classen-Linke et al. *Cell Tissue Res.* 287(1) 171-185 (1997); Gerschenson et al. *Pathol. Res. Pract.* 174(3): 285-296 (1982)) are the most commonly used for characterization.

In a preferred embodiment, cells can be characterized using cell specific antibodies. This can be done by transferring and culturing the cells onto chamber slides, fixed with 4% buffered formaldehyde, and processing. The cells can be exposed to antigen-specific primary antibodies applied to the surface of the cell. Non-limiting examples of cell specific antibodies are the broadly reacting anti-cytokeratin and anti-smooth muscle α-actin antibodies. Negative controls can be treated with plain serum instead of primary antibody. Positive controls will consist of antigen exposed cells. After washing with phosphate-buffered saline, the chamber slides can be incubated with a biotinylated secondary antibody and washed again. A peroxidase reagent can be added and, upon substrate addition, the sites of antibody deposition will be visualized as a brown precipitate. Counterstaining can be performed with Gill's hemotoxylin.

Any type of molecular characterization well known in the art can be employed. In a preferred embodiment, Western blot analysis can be used for cell characterization at a molecular level using antibodies to the area of interest. For example, monoclonal antibodies α-actin, myosin, and cytokeratins AE1/AE3 can be used to compare protein expression with cells and controls cultured in vitro to confirm the maintenance of epithelial and smooth muscle cell lines. The cells can be homogenized in cold lysis buffer and the soluble protein supernatant collected. Any method of protein quantification known in the art can be used. For example, BioRad DC protein assay kit can be used for quantification of the protein samples. Equal concentrations of protein can be loaded and separated on SDS-PAGE gel and probed overnight at 4° C. with the primary antibody. Peroxide-conjugated anti-mouse secondary antibody is complexed and detected with an enhanced chemiluminescent system. Polymerase chain reactions can also be concomitantly performed for additional qualification of the cell types.

V. Polylayers a. Formation of Polylayers on a Decellularized Structure

In one embodiment, different cultured cell populations can be used to produce different polylayers on a biocompatible matrix or decellularized structure, for example a decellularized organ, or a part of an organ. A first homogenous cell suspension can be perfused into the decellularized structure using needles embedded within localized positions of the three-dimensional infra-structure of the decellularized organ. The perfused cells distribute between the three-dimensional interstices of the infra-structure and grow to produce a layer of cells that envelopes the infra-structure. After perfusion of the first homogenous cell suspension, the decellularized organ is incubated in culture medium at 37° C. until the cells develop and proliferate to produce a monolayer of a first population of cultured cells that is attached to the infra-structure of the decellularized organ. Once the monolayer is established, the first homogenous cell suspension is again perfused into the decellularized structure over the monolayer. The decellularized organ is incubated until the cells develop and proliferate to produce a second monolayer of cells over the first monolayer, thereby producing a bilayer. The process is repeated until a polylayer of a first homogenous cell population is produced.

The first polylayer resembles the functional characteristics and morphology of the equivalent parenchyma tissue of an in vivo organ. For example, with a decellularized uterus, the first cell population is a smooth muscle cell population. The smooth muscle cell suspension is perfused into the uterus, vagina, fallopian tube or cervix until a polylayer of smooth muscle tissue is formed, which has the functional characteristics that resemble smooth muscle tissue (i.e. the myometrium) of a uterus, vagina, fallopian tube or cervix.

After creating the first polylayer, a second polylayer is created using a second cultured cell population that is different form the first cell population. A cell suspension of the second homogenous cell population is perfused onto the first polylayer in the decullularized organ. The perfused cells distribute along the first polylayer, and the decullularized organ is incubated until the cells of the second cell population develop and proliferate into a first monolayer. Once the first monolayer is established, the second homogenous cell population is again perfused into the decellularized structure over the first monolayer. The decellularized organ is incubated until the cells develop and proliferate to produce a second monolayer over the first monolayer thereby producing a bilayer. The process is repeated until a second polylayer of a second homogenous cell population is produced.

The second polylayer resembles the functional and morphological characteristics of the equivalent parenchyma tissue of an in vivo organ. For example, the second polylayer for the uterus, vagina, fallopian tube or cervix is an epithelial polylayer which resembles the morphological and functional characteristics of the epithelial tissue (i.e., the mucosa) of the uterus, vagina, fallopian tube or cervix.

The skilled artisan will appreciate that a number of heterogenous polylayers can be produced to create artificial female reproductive organs. Each polylayer comprises multiple layers of a homogenous cell population, although the cell populations of the polylayers are different. In one embodiment, the artificial organ comprises at least about five polylayers. In another embodiment, the artificial organ comprises at least about four polylayers. In yet another embodiment, the artificial organ comprises at least about three polylayers. In a preferred embodiment, the artificial organ comprises at least about two polylayers.

A chimeric interface is produced where two or more heterogenous polylayers are in mutual contact with each other. This enables unhindered interaction to occur between the cells of the polylayers. Extensive interactions between different cell populations results in the production of a interstitial biomaterial which is different from each of the polylayers. As the interaction between the two different cell populations is not hindered by structural barriers such as, biocompatible substrates (e.g. polymers), the cells at the chimeric interface resume a more natural shape and configuration. By providing a microenvironment at the chimeric interface that is more conducive to the microenvironment of an in vivo organ, the cells at the chimeric interface develop more naturally and produce growth factors and other proteins which promote normal division and differentiation. This can result in the production of interstitial biomaterial that provides unique biological and functional properties to create artificial organs that more closely resemble those found in the in vivo. For example, interaction of the smooth muscle polylayer and the epithelial polylayer of an artificial uterus, vagina, fallopian tube or cervix produces a chimeric interface resulting in the production of a layer of cells that resembles the submucosa of an in vivo uterus, vagina, fallopian tube or cervix. The submucosa provides functional characteristics that are unique from those of the smooth muscle cells and the epithelial cells, in that the submucosa when fully developed provide a blood supply to the smooth muscle cells.

The skilled artisan will appreciate that any interstitial biomaterial produced when two or more heterogenous polylayers comprising different cell populations interact, is within the scope of the invention. The different interstitial biomaterial produced will depend on the type of cells in the heterogenous polylayer.

In one embodiments, additional collagenous layers may be added to the inner surfaces of the decellularized structure to create a smooth surface as described in International PCT Publication No. WO 95/22301, the contents of which are incorporated herein by reference. This smooth collagenous layer promotes cell attachment which facilitates growth and development. As described in International PCT Publication No WO 95/22301, this smooth collagenous layer may be made from acid-extracted fibrillar or non-fibrillar collagen, which is predominantly type I collagen, but may also include type II collagen, type IV collagen, or both. The collagen used may be derived from any number of mammalian sources, typically pig and cow skin and tendons. The collagen preferably has been processed by acid extraction to result in a fibril dispersion or gel of high purity. Collagen may be acid-extracted from the collagen source using a weak acid, such as acetic, citric, or formic acid. Once extracted into solution, the collagen can be salt-precipitated using NaCl and recovered, using standard techniques such as centrifugation or filtration. Details of acid extracted collagen are described, for example, in U.S. Pat. No. 5,106,949 issued to Kemp et al., incorporated herein by reference.

In another embodiment, additional collagenous layers may be added between the heterogenous polylayers to promote growth and development between the cells of heterogeneous polylayers. In yet another embodiment, factors such as nutrients, growth factors, cytokines, extracellular matrix components, inducers of differentiation or products of secretion, immunomodulation, biologically active compounds which enhance or allow growth of the cellular network or nerve fibers can be added between the heterogenous polylayers.

b. Formation of Polylayers on a Polymer Substrate

In another embodiment, different cultured cell populations can be used to produce heterogenous polylayers on one area of a polymer. Examples of suitable polymers include, but are not limited to, collagen, poly(alpha esters) such as poly(lactate acid), poly(glycolic acid), polyorthoesters and polyanhydrides and their copolymers, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyestercarbonate, polyether, polyetheretherketone, polyetherimide, polyetherketone, polyethersulfone, polyethylene, polyfluoroolefin, polylmide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends of these materials.

In a preferred embodiment, one side of the biocompatible substrate is used to create a polylayer of a first homogenous cell population. This is performed by coating one side of the biocompatible substrate with a suspension of a first homogenous cell population, e.g., smooth muscle cells. The first homogenous cell suspension is incubated in culture medium until the cells develop and proliferate to produce a monolayer and cells of the monolayer attach to the biocompatible substrate. Once the monolayer is established, the first homogenous cell suspension is deposited over the first monolayer, and the cells are cultured until they develop and proliferate to produce second monolayer of cells over the first monolayer, thereby producing a bilayer. The process is repeated until a polylayer comprising multiple layers of the first homogenous cell population is generated. The first polylayer has morphological and functional characteristics that resemble the tissue of an in vivo organ.

After the first polylayer is established, a second polylayer comprising a second homogenous cell population is created, (e.g., epithelial cell population) over the first polylayer. This produces a chimeric interface between the two different cell populations. The second polylayer is created by depositing a cell suspension of a second homogenous cell population onto the first polylayer. The cells of second homogenous cell population are cultured until they develop and proliferate to produce a first monolayer. Once the first monolayer is established, the second homogenous cell suspension is deposited over the first monolayer, and the cells are cultured until they develop and proliferate to produce a second monolayer of cells over the first monolayer, thereby producing a bilayer. The process is repeated until a second polylayer comprising multiple layers of a second homogenous cell population is generated. The second polylayer has morphological and functional characteristics that resembles the parenchyma tissue of an in vivo organ e.g., the mucosa. An interstitial biomaterial is produced at the chimeric interface between the two different cell populations, as described above.

In one embodiment, smooth muscle cells, e.g., myometrial cells, are perfused on one side of a biocompatible matrix forming a polylayer and female reproductive epithelial cells, e.g. endometrial cells, are perfused on the opposite side of a biocompatible matrix forming a second polylayer. The biocompatible matrix forms the submucosa. The biocompatible matrix may be biodegradable allowing the two cell populations to form a chimeric interface.

The invention therefore provides compositions and methods of producing artificial organs with a multicellular organization that more closely resemble that of a native in vivo organ. The cellular organization includes heterogenous polylayers. Each polylayer of the artificial female reproductive organ comprises multiple layers of a homogenous cell population, generating an organized structure with a cellular morphology and functional characteristics that resemble the equivalent tissue native in vivo layers of a natural organ.

The chimeric interface between the different polylayers provides a microenvironment that mimics the native microenvironment between different cell populations. The skilled artisan will appreciate that cell shape plays an important role in cell division and differentiation (see e.g., Darnell et al. Molecular Cell Biology (1986) published by Scientific American Books). The more natural microenvironment created by the method of the invention, permits mutual, dynamic, unhindered cell-cell interactions between cells of the heterogenous polylayers. These unhindered interactions enable the cells at the interface to resume a more natural cellular and morphological configuration. The more natural cell development at the chimeric interface enables the cells to produce proteins which promote normal division and differentiation.

VI. In vivo Implantation

Grafting of female reproductive artificial organs can be performed according to art-recognized methods (See e.g., Fauza et al. (1998) *J. Ped. Surg.* 33: 7-12). For example, the artificial female organ may be implanted vaginally, pelvically, transurgically, or through the suprapubic region, abdomen, or rectum.

In one embodiment, the artificial uterus is sutured to the fallopian tubes and the vagina. The fallopian tubes enter the uterus at its upper corners; the lower, narrowed portion, the cervix, projects into the vagina. A normal uterus is tilted slightly forward and lies behind the urinary bladder. In a preferred embodiment, a small section at each end of the native uterus remains such that the artificial uterus may be sutured to the remaining portion of the native uterus. In one embodiment, at least 10% of the native uterus remains at each side so that the artificial uterus may be sutured to the remaining native uterine structure. In another embodiment, the artificial uterus is sutured to the uterosacral ligaments such that the cervix is tethered to the sacrum and the 90° angle between the longitudinal axes of the vagina and the uterus is maintained.

In another embodiment, the artificial vagina is sutured to the uterus. In another embodiment, the artificial vagina is sutured to the cardinal, or transverse cervical, ligaments, which extend from the lateral pelvic walls to the cervix. Suturing to the cardinal ligaments will stabilize the midline position of the cervix and the vault of the vagina.

In another embodiment, the artificial fallopian tubes are sutured to the uterus and the ovary. The artificial fallopian tube is sutured on one side to the caudal end of the uterus and at the other side it is sutured at or near an ovary.

In another embodiment, the artificial ovary is sutured to the uterus. In another embodiment, the artificial ovary is sutured to the peritoneal ligament, the mesovarium, which attaches to the posterior peritoneum layer of the broad ligament of the uterus.

VII. Uses of the Artificial Female Reproductive Organs

The artificial female reproductive organs of the invention can be used in a variety of applications. For example, the reconstructed artificial female reproductive organs can be implanted into a subject. Implants, according to the invention, can be used to replace or augment existing tissue; for example, to treat a subject with congenital vaginal anomalies and cloacal malformations. For example, the subjects with the anomalies, such as an absent or unilateral absent ovarian structure, absent fallopian tube and vaginal atresia, and bicomuate uterus, may be treated with the methods and compositions of the present invention. Additionally, subjects with cancer may choose to have their organs replaced to prevent metastases. The subject can then be monitored for amelioration of the anomalies.

The methods and constructions of the present invention may be used an alternative treatment to a variety of disorders. For example, hysterectomies are currently used for the treatment of a variety of disorders including fibroids, endometriosis or chronic pelvic pain, bleeding problems, uterine prolapse, as well as cancer of the uterus, ovaries or cervix. Hysterectomy, the surgical removal of the uterus, can occur in two types: total (complete), in which the uterus and the cervix is removed, or subtotal (supracervical), in which the uterus is removed while the cervix remains. In some cases the ovaries or fallopian tubes will also be removed. In one embodiment, artificial female organs, tissues, or segments thereof can be implanted into the patient to replace the removed organs.

The methods and compositions of the present invention can be used to reduce infertility. Infertility in women can be caused by many different problems including, but not limited to, Polycystic ovarian syndrome (PCOS), polycystic ovaries, inability to produce eggs, anovulation, endometriosis, blockage of the fallopian tubes, scarring of the uterus, and the inability to produce cervical mucous of sufficient quantity or quality. In one embodiment, the methods of the present invention can be used to modulate hormone levels. FSH (follicle stimulating hormone) may stimulate ovulation in women. In another embodiment, a scarred female reproductive organ may be replaced with a functioning artificial organ.

In one aspect, the invention provides a method of reducing infertility in a subject comprising providing a biocompatible matrix, perfusing a first cell population on or in the biocompatible matrix, the first cell population being substantially a uterine epithelial cell population, perfusing a second cell population of a different cell type than the first cell population on or in the biocompatible matrix, culturing the cell populations in the biocompatible matrix, such that an artificial uterus is formed, depositing a fertilized egg in the artificial uterus, implanting the artificial uterus in the subject, to thereby create an artificial uterus in the subject, whereby the artificial uterus supports the growth of the deposited fertilized egg.

Endometriosis, the presence of endometrial tissue outside the uterus, can cause infertility in women especially when the ovaries or fallopian tubes are involved. This infertility may be due to the adhesions, or scar tissue, that can form and block the fallopian tubes preventing the egg from entering the uterus. The methods of the present invention can be used to regrow female reproductive tissue, organs, or segments thereof to restore fertility. The methods and compositions of the invention can be used, for example, to create an artificial fallopian tube such that the subject can ovulate effectively. In another embodiment, an artificial uterus can be created that is capable of supporting the growth of fetus. In one embodiment, a fertilized egg may be implanted into the artificial fallopian tube, in vitro or in vivo.

In yet another embodiment, the methods and compositions of the present invention can be used to improve in vitro culture of embryos. Due to imperfect in vitro fertilization culture conditions, only about 20-40% of human embryos will progress to the blastocyst stage after 5 days of culture. Currently, to increase the chances of progression to a blastocyst, embryos are being transferred from in vitro culture into the uterus after only 2-3 days of culture. However, under natural in vivo conditions 2 to 3 day old embryos are normally found in the fallopian tubes, not in the uterus. The present invention can provide an alternative to current in vitro culture conditions.

In one embodiment, the embryo can be implanted into an artificial fallopian tube, either in vitro or in vivo. The embryo can then be transplanted into the uterus following further maturation in the artificial fallopian tube. In nature, the embryo moves from the fallopian tube into the uterus at about 80 hours after ovulation. Approximately three days later, following blastocyst formation and hatching, implantation into the uterus occurs. A blastocyst, an embryo that has developed for five to seven days after fertilization, has two different cell types, a central cavity, and has just begun to differentiate. The surface cells, called the trophectoderm, will become the placenta, and the inner cells, called the inner cell mass, will become the fetus. By the end of the sixth day, a blastocyst should begin hatching from its outer shell, called the zona pellucida. Within about 24 hours after-hatching, it should begin to implant into the lining of the uterus. The present invention will allow a blastocyst to develop prior to implantation in the uterus. In another embodiment, conception can occur naturally resulting in blastocyst implantation into an in vivo artificial uterus.

In one embodiment, the methods and compositions of the present invention can be used to construct an artificial fallopian tube in a subject in order to reverse a tubal ligation. A portion of the fallopian tube is removed in a Pomeroy procedure. This procedure is performed with a cesarean section or in the immediate post-partum period after a vaginal birth. A laparoscopic tubal ligation may be performed by cauterizing a segment of each fallopian tube, by placing a clip across the fallopian tubes, or by placing a small ring around a portion of the tubes. The common result is that the tube is blocked, thereby preventing the normal transport of egg and sperm. The reversibility of this procedure depends on the length of available fallopian tube for reconstruction (reanastomosis). An artificial fallopian tube or section thereof can be sutured to the remaining fallopian tube such that normal function is restored and the subject can conceive.

The reconstructed artificial female reproductive organs can be used in vitro to screen a wide variety of compounds, for effectiveness, cytotoxicity, and/or the therapeutic effect of pharmaceutical agents, chemical agents, growth/regulatory factors. The cultures can be maintained in vitro and exposed to the compound to be tested. The activity of a cytotoxic compound can be measured by its ability to damage or kill cells in culture. This may readily be assessed by vital staining techniques. Cytotoxic compounds may be useful as an abortive method. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the reconstructed artificial female reproductive organs may be assessed.

In one embodiment, the reconstructed artificial female reproductive organs can be used in vitro or in vivo to screen a wide variety of compounds that modulate smooth muscle cells. Contraction of smooth muscles can be through paracrine stimulation, through substances that are released in the proximity of the smooth muscles, or though hormones that circulate in the blood, such as oxytocin that stimulates uterine contraction during childbirth. While smooth muscle cells do not require motor neurons for stimulation, neurotransmitters released by motor neurons, such as noradrenaline and nitric oxide, can stimulate or relax smooth muscle. Thus, a wide variety of compounds may have an effect on smooth muscle cell contraction. In one embodiment, compounds that induce contraction may be screened. Such compounds may be useful to stimulate childbirth.

The reconstructed artificial female reproductive organs of the invention may be used as a vehicle for introducing genes and gene products in vivo to assist or improve the results of the transplantation and/or for use in gene therapies. For example, the cultured artificial female reproductive cells can be engineered to express gene products. The cells can be engineered to express gene products transiently and/or under inducible control or as a chimeric fusion protein anchored to the artificial female reproductive cells, (e.g., vaginal epithelial cells) for example, a chimeric molecule composed of an intracellular and/or transmembrane domain of a receptor or receptor-like molecule, fused to the gene product as the extracellular domain. In another embodiment, the female reproductive cells can be genetically engineered to express a gene for which a patient is deficient, or which would exert a therapeutic effect. The genes of interest engineered into the female reproductive cells need to be related to the disease being treated. For example, for a vaginal disorder, the cultured vaginal epithelial cells can be engineered to express gene products that would ameliorate the vaginal disorder.

The female reproductive cells, e.g., vaginal epithelial cells can be engineered using a recombinant DNA construct containing the gene of interest which is used to transform or vaginal epithelial cells. The three-dimensional scaffold and vaginal tissue layer which expresses the active gene product, could be implanted into an individual who is deficient for that product. For example, genes that prevent or ameliorate symptoms of various types of female reproductive abnormalities may be underexpressed or down regulated under disease conditions. The level of gene activity may be increased by either increasing the level of gene product present or by increasing the level of the active gene product which is present in the three-dimensional scaffold and vaginal epithelial cells. The three-dimensional culture which expresses the active target gene product can then be implanted into the patient who is deficient for that product.

The three-dimensional cultures containing such genetically engineered female reproductive tissue are then implanted into the subject to allow for the amelioration of the symptoms of the disease. The gene expression may be under the control of a non-inducible (i.e., constitutive) or inducible promoter. The level of gene expression and the type of gene regulated can be controlled depending upon the treatment modality being followed for an individual patient.

Other embodiments and used of the invention will be apparent to those skilled in the art from consideration of the specification and practice of the invention disclosed herein. All U.S. patents and other references noted herein for whatever reason are specifically incorporated by reference. The specification and examples should be considered exemplary only with the true scope and spirit of the invention indicated by the following claims.

EXAMPLES

The successful creation of prefabricated organs in the laboratory from autologously derived cells that are phenotypically normal can result in normal functional development. The following examples illustrate that the methods and compositions of the present invention can be employed to harvest cells, preferably autologous cells, expand them in vitro, and subsequently implant them in vivo at a site requiring reconstruction, repair, augmentation, or replacement. The invention is demonstrated in the following examples in which a reconstituted, viable vagina, fallopian tube, and uterus is created in vivo. The following examples are merely illustrative of the present invention and should not be construed so as to limit the scope of this invention.

Example 1

Materials and Methods for Creating an Artificial Vagina (i) Tissue Harvest and Cell Culture New Zealand White rabbits served as the donor source of vaginal tissue. The animals were anesthetized with intramuscular Ketamine (25 mg/kg), Xylazine (2 mg/kg), and Acepromazine (0.75 mg/kg). The lower abdomen was prepared in a sterile manner with a povidone-iodine (Betadine) solution.

The vaginal tissue (1 cm$^2$) and fallopian tube tissue were harvested through a simple, midline, transabdominal approach allowing for good exposure during the biopsy. The retrieved tissue was washed several times and the muscle and epithelial tissues were separated by microdissection or enzymatic digestion.

Smooth muscle cells were extracted using the explant method. Several muscle strips were carefully dissected from the seromuscular layer of the tissue under loop magnification. These pieces were individually placed onto culture dishes and then incubated with Dulbecco's Modified Eagle's Medium (DMEM, Mediatech Inc, Herndon, Va.) supplemented with 10% Fetal Bovine Serum (FBS, Life Technologies, Rockville, Md.) at 37° C. in air and 5% $CO_2$, and were left undisturbed until a sufficient colony of cells grew from the tissue islets. The explants were removed by gentle suction and the cells were maintained with scheduled replacement of the medium every 24 to 48 hours.

Epithelial cells can be isolated from the vaginal and fallopian tube specimens by enzymatic digestion using collagenase type IV (Worthington Biochemical Corportation, Lakewood, N.J.) and Dispase (Boehringer Mannheim, Indianapolis, Ind.). The tissue was immersed into the enzymatic solution, and vigorously shaken for 30 minutes at 37° C. With gentle pipette suction, the cell/fluid suspension was centrifuged at low revolutions for 5 minutes. The supernatant was resuspended in Keratinocyte Serum Free medium (K-SFM, Life Technologies, Rockville, Md.) and distributed into culture dishes and maintained with K-SFM with medium changes every 24 to 48 hours. Each cell type was expanded to approximately fifty 15 cm polystyrene culture dishes to achieve a desired cell density of $10 \times 10^6$ cells/cc for epithelial cells and $20 \times 10^6$ cells/cc for smooth muscle cells.

(ii) In vitro Cell Characterization Histology and Immunohistochemistry

Vaginal or fallopian tube epithelial and smooth muscle cells were seeded onto chamber slides and fixed with 4% buffered formaldehyde and processed after an appropriate colony number had been established in culture. Broadly reacting cytokeratin (Boehringer Mannheim, Indianapolis, Ind.) and smooth muscle alpha actin antibodies (Novocastra, Newcastle, UK) were used to confirm the epithelial and smooth muscle cell phenotypes, respectively. Theses cells were compared to negative controls incubated with blocking solution instead of primary antibody. After washing with phosphate buffered saline, the cells were incubated with a biotinylated secondary antibody and washed prior to development with a peroxidase reagent. Counterstaining was performed with Gill's hematoxylin.

(iii) Cell Seeding and in vivo Implantation (a) The following protocol was followed in Example 2. Polyglycolic Acid (PGA) scaffolds were coated with a 50:50 copolymer of Poly(DL-Lactide-CO-Glycolide). The scaffolds were sterilized with ethylene oxide gas and pre-wetted with medium 24 hours prior to seeding with cells. Both the vaginal epithelial and smooth muscle cells were seeded onto opposite sides of sixty scaffolds in a staggered fashion at a concentration of $10 \times 10^6$ cells/cc and $20 \times 10^6$ cells/cc, respectively. The cells were cocultured at 37° C. with 5% $CO_2$ for 24 to 48 hours. Eighty scaffolds, 60 seeded with cells and 20 unseeded, were implanted subcutaneously in mice. Mice received both Ketamine (25 mg/kg) and Xylazine (5 mg/kg) for sedation, followed by Buprenex (0.1 mg/kg) and a cephlasporin postoperatively for pain control and antibiotic prohylaxis. Each mouse was implanted with 3 cell-seeded and 1 unseeded scaffold. The animals were sacrificed at 1, 4, and 6 weeks after implantation.

(b) In Example 3, the following protocol was followed. Polyglycolic Acid (PGA) (Albany International, Mansfield, Mass.) scaffolds were coated with a 50:50 copolymer of Poly(DL-Lactide-CO-Glycolide). These scaffolds were preconfigured and tabularized prior to cell seeding. Both the vaginal epithelial and smooth muscle cells were dynamically seeded in a bioreactor system at a concentration of $10 \times 10^6$ cells/cc and $20 \times 10^6$ cells/cc, respectively. The cells were cocultured at 37° C. with 5% $CO_2$ 7 days prior to implantation into the rabbits. Six animals were implanted with unseeded scaffolds and 9 animals were implanted with seeded scaffolds. The rabbits received Ketamine (25 mg/kg) and Xylazine (5 mg/kg) for sedation, followed by Buprenex (0.1 mg/kg) and a cephlasporin postoperatively for pain control and antibiotic prohylaxis. Animals were sacrificed at 1, 4, and 6 months after implantation.

(iv) Immunocytochemical and Histologic Analyses of Seeded Scaffolds

Five-micrometer sections of formalin-fixed paraffin-embedded tissues were processed and stained with hematoxylin-eosin and Mason's trichrome. Epithelial cell layers were identified using broadly reacting monoclonal anti-pancytokeratins AE1/AE3. Smooth muscle fibers were labeled with monoclonal α-smooth muscle actin antibodies. Immunolabeling was performed using the avidin-biotin detection system and sections were counterstained with hematoxylin. Sections of normal vaginal tissue were also stained as positive controls for comparison.

(v) Molecular Analysis

Western Blot Analyses with monoclonal antibodies α-actin and cytokeratins AE1/AE3 were used to compare protein expression between native vaginal tissue which served as a control and the reconstituted vaginal structures in order to confirm the maintenance of epithelial and smooth muscle cell phenotypes. Tissues were homogenized in cold lysis buffer and the soluble protein supernatant collected. Quantification of the protein samples was done using a bioRad DC protein assay kit. Equal concentrations of protein were loaded and separated on SDS-PAGE gels and probed overnight at 4° C. with the primary antibody. In Example 2, peroxidase conjugated anti-mouse secondary antibody was complexed and detected with an EHL chemiluminescence system.

(vi) Organ Bath Studies

A longitudinal strip of native and tissue engineered vagina were compared with organ bath analyses. The strips were attached by 4-0 silk sutures to a tissue support hook at one end and an isometric force transducer (Radnoti Glass Technology, Monrovia, Calif.) at the other end. The specimens were mounted in isolated baths containing 50 mL of Tyrode's solution equilibrated with 95% $O_2$, 5% $CO_2$ supplied by a bubbling chamber and maintained at 37° C. Peak contractions were recorded for each individual strip of tissue exposed to a variety of electrical and chemical stimuli. Transducer signals were fed into a recorder. For electrical field stimulation, two 10 mm diameter ring platinum iridium electrodes were used with a Grass S48 stimulator (AstroMed, Inc., Warick, R.I.). The tissues were mounted at a preload tension of 20 mNewton (2.0 gm), resulting in a resting tension of about 8 mNewton (0.8 gm) at the end of a 60 minute equilibration period.

Serial field stimulation was applied (20, 40, and 60 Hz; 100 volts, 1 msec duration square pulses) with 3 minutes of resting intervals between stimulations, and active tension was measured. To confirm the expression and function of neurotransmitter receptors, specific autonomic agonists were used (carbachol and phenylephrine).

Example 2

Preparation of a Tissue Engineered Vagina

Congenital vaginal anomalies and cloacal malformations may require extensive surgical construction. Surgical challenges are often encountered due to the limited amount of native tissue available. Currently, non-reproductive tract tissues are being used for vaginal construction, despite a number of associated complications. Autologous vaginal tissue are preferable. This example describes the use of vaginal epithelial and smooth muscle cells for the engineering of vaginal tissues in vivo.

Vaginal epithelial (VE) cells and smooth muscle cells (SMC) of female rabbits were grown and expanded in culture. Both cell types were characterized immunocytochemically. Vaginal epithelial cells and smooth muscle cells were seeded onto polymers of polyglocolic acid (PGA) at $10\times10^6$ cells/$cm^3$ and $20\times10^6$ cells/$cm^3$, respectively. The cell seeded scaffolds were subcutaneously implanted into nude mice. The animals were sacrificed at 1, 4, and 6 weeks after implantation. Immunocytochemical and histochemical analyses were performed with pancytokeratins AE1/AE3, and smooth muscle specific alpha-actin antibodies to confirm the reconstituted tissue phenotype. Western blot analyses and electrical field stimulation studies were also performed to further characterize the tissue engineered constructs both at a molecular and functional level.

The results demonstrate that both vaginal epithelial and smooth muscle cells were positively identified immunocytochemically and maintained at all culture stages in vitro, thereby confirming the preservation of both epithelial and smooth muscle phenotypes prior to seeding onto the polymer matrices. Vaginal epithelial cells were identified with anti-pancytokeratins AE1/AE3 and the smooth muscle cells stained positively for α-smooth muscle actin antibodies at all culture stages in the nude mice.

Grossly, the retrieved polymer scaffolds resembled normal appearing tissue on inspection and in texture. Histologically the retrieved scaffolds demonstrated multilayered tissue strips by 1 week after implantation that continued to demonstrate progressive organization to a distinguishable layer for both the vaginal epithelial and smooth muscle cell types over 6 weeks. A hematoxylin and eosin stain (100×) of the vaginal epithelial and smooth muscle cell seeded scaffolds that had been implanted in vivo and retrieved at 6 weeks cells of normal vaginal tissue. The presence of a complete transitional cell layer of vaginal epithelial cells was confirmed immunocytochemically with the broadly reacting anti-pancytokeratins AE1/AE3 in all implants. Vaginal epithelial cells stained positive for cytokeratine AE1/AE3 (200×). Smooth muscle cells stained positively for α-smooth muscle actin specific antibodies (200×) and demonstrated an increased number of organized muscle bundles over time. Penetrating native vasculature was also noted. There was no evidence of tissue formation in the controls. The same primary antibodies were employed for Western Blot analyses which confirmed the presence of normally differentiated epithelial and smooth muscle cells in the tissue engineered scaffolds seeded with cells. A western blot of cell-seeded scaffolds demonstrates protein bands for both cytokeratin AE1/AE3 and α-smooth muscle actin at 1, 4, and 6 weeks after implantation. The corresponding protein bands were seen for both epithelial and smooth muscle cells for all reconstituted tissue structures and at all time points when compared to controls.

Contractile responses were observed in the tissue engineered constructs when electrically stimulated. FIG. 1 demonstrates the evoked potentials at various levels of electrical stimulation for both normal and tissue engineered vagina 6 weeks after implantation. Similar amplitudes of response were observed between the tissue engineered constructs and normal vaginal tissue at a stimulus duration of 3 seconds with 100 V and frequencies of 20 Hz, 40 Hz, and 60 Hz. Although the initial evoked response was similar between tissue engineered vaginal tissue and normal vaginal tissue, the recovery phase in the tissue engineered constructs took longer (avg=7 sec) than normal tissue (1.5 sec) to reach baseline. No induced responses were observed in the tissue engineered constructs to chemical stimulation with carbachol or phenylephrine.

Vaginal cells were readily propagated in vitro to very large colony counts prior to seeding onto polymer scaffolds of PGA. Both cell types, epithelium and smooth muscle, maintained expression of their individual phenotypes at all stages of culture, as confirmed by immunocytochemical staining with pancytokeratins AE1/AE3 and α-actin smooth muscle antibodies, respectively. The ability to replicate in vitro rapidly and to large cell counts with no infringement on normal phenotype is a desirable feature for the successful engineering of tissue.

The vaginal epithelial and smooth muscle cells were successfully cocultured on the PGA constructs. When implanted in vivo the vaginal cells could be successfully identified phenotypically as either epithelial or smooth muscle, by both immunocytochemical and western blot analyses. Moreover, the tissue engineered constructs demonstrated a progressive architectural organization over time towards normal transitional layers for both the epithelial and smooth muscle components. These findings imply that vaginal epithelial and smooth muscle cells can replicate and survive in vivo for prolonged periods and can self organize towards a normal structural orientation.

Functionally, the tissue engineered vaginal constructs were capable of producing contractile forces similar to those seen with native vaginal tissue when stimulated with a series of electrical impulses. This would seem to imply an intact structural membrane system that allows for cell depolarization and the release of intracellular cations that are converted into a contractile force. Differences were noted in the recovery phase, between native and engineered vaginal tissue. There was no response to chemical stimulation with either muscarinic or adrenergic agonists. These findings imply that the neurotransmitter receptor complex was not fully developed for the time encompassed in the experiment, which was only 6 weeks at the longest time point. These findings are consistent with the functional profile seen in other tissues, such as bladder and urethra, where a response to electrical stimulation is seen after 4 weeks but chemical stimulation parameters are not seen until after 3 months of tissue development.

The data shows that vaginal epithelial cells and smooth muscle cells can be easily cultured and expanded in vitro. Cell seeded polymer scaffolds are able to form vascularized vaginal tissue in vivo that have similar phenotypic and functional properties to normal vaginal tissues. This study demonstrates the use of the present invention wherein vaginal epithelial cells and smooth muscle cells are reconstituted in vivo into vaginal tissue. This technology may be pursued in order to achieve the engineering of vaginal tissues for clinical applications.

Example 3

Complete Vaginal Replacement in Large Animals Using Tissue Engineered Constructs The following study demonstrates that vaginal epithelial and smooth muscle cells can replicate and survive in vivo in rabbits for prolonged periods and can self organize towards seemingly normal structural orientation that are capable of producing contractile forces similar to those seen with native vaginal tissue.

Autologous vaginal epithelial (VE) cells and smooth muscle cells (SMC) of female rabbits were grown and expanded in culture. Both cell types were confirmed immunocytochemically prior to seeding the polymers. A Coculture VE and SMC's were dynamically seeded onto polymers of polyglocolic acid (PGA) at concentrations of $5 \times 10^6$ cells/cm$^3$ in bioreactors. A total of 15 animals were used for this experiment. Cell seeded scaffolds were used for complete vaginal replacement in 9 animals while unseeded constructs were used for replacement in 6 animals as controls. Vaginograms were performed at 1, 3, and 6 months after implantation. Animals were also sacrificed at 1, 3, and 6 months for analyses. Immunocytochemical and histochemical analyses were performed with pancytokeratins AE1/AE3, and smooth muscle specific alpha-actin antibodies to confirm the reconstituted tissue phenotype. Western blot analyses and electrical field stimulation studies were also performed to further characterize the tissue engineered constructs both at a molecular and functional level. Contractility and the presence of neurotransmitter receptors were confirmed with organ bath studies. Fluorescent cell membrane label (Sigma-Aldrich, St Louis, Mo.) was used to confirm cell viability in vivo.

After implantation, all of the unseeded grafts collapsed or developed strictures by 1 month. Serial vaginography of the unseeded polymers demonstrated the presence of strictures. In contrast, serial vaginography confirmed the maintenance of a wide vaginal caliber without any signs of strictures in animals implanted with seeded tubularized polymers. Grossly, the retrieved seeded scaffolds resembled normal appearing tissue on inspection and in texture without any evidence of fibrosis.

Histologically, a transitional cell layer surrounded by muscle cell fiber bundles with increasing cellular organization over time were observed on the cell seeded constructs. The retrieved scaffolds demonstrated multilayered tissue strips by 1 month after implantation that continued to demonstrate progressive organization to a distinguishable layer for both the vaginal epithelial and smooth muscle cell types over time. Cell viability and organization was also confirmed with cell membrane labeling techniques. The presence of a complete transitional cell layer of vaginal epithelial cells was confirmed immunocytochemically with the broadly reacting anti-pancytokeratins AE1/AE3 in all implants. The same was observed with smooth muscle cells which stained positively for α-actin specific antibodies and demonstrated an increased number of organized muscle bundles over time. Similar staining patterns and intensity were observed when the reconstituted structures were compared to positive controls of normal vaginal tissue. Penetrating native vasculature was also noted. The same primary antibodies were employed for Western Blot analyses which confirmed the presence of normally differentiated epithelial and smooth muscle cells in the tissue engineered scaffolds seeded with cells. The corresponding protein bands were seen for both epithelial and smooth muscle cells for all reconstituted tissue structures and at all time points (1, 3, and 6 months) when compared to controls. In contrast, a transitional cell layer with scant unorganized muscle fiber bundles and large areas of fibrosis were present on the unseeded constructs.

Specific agonists (carbachol and phenylephrine) were used to confirm functionally the presence of muscarinic and adrenergic receptors in the engineered and normal urethral walls. Addition of carbachol ($10^{-6}$ M) and phenylephrine ($10^{-3}$ M) elicited qualitatively identical contractions in the engineered and the normal vaginal strips. The tissue engineered vaginal tissue proved capable of generating contractile forces through neurotransmitter-based mechanisms. A functional electrochemical response was observed with the tissue engineered constructs electric field stimulation and organ bath studies. The electrical field stimulation demonstrated similar responses in contraction in the tissue engineered constructs when compared to normal vagina.

In this study, vaginal cells were successfully cultured in vitro and used to create reconstituted, viable tissue in vivo. Vaginal cells were readily propagated in vitro to very large colony counts prior to seeding onto polymer scaffolds of PGA. Both cell types, epithelium and smooth muscle, maintained expression of their individual phenotypes at all stages of culture, as confirmed by immunocytochemical staining with pancytokeratins AE1/AE3 and α-actin smooth muscle antibodies, respectively. The ability to replicate in vitro rapidly and to large cell counts with no infringement on normal phenotype is a desirable feature for the successful engineering of tissue.

Vaginal epithelial and smooth muscle cells were successfully cocultured on the PGA constructs. When implanted in vivo the vaginal cells could be successfully identified phenotypically as either epithelial or smooth muscle, by both immunocytochemical and western blot analyses. Moreover, the tissue engineered constructs demonstrated spatial orientation over time towards distinctive transitional layers for both the epithelial and smooth muscle components. These findings imply that vaginal epithelial and smooth muscle cells can replicate and survive in vivo for prolonged periods and can self organize towards seemingly normal structural orientation.

Functionally, the tissue engineered vaginal constructs were capable of producing contractile forces similar to those seen with native vaginal tissue when stimulated with a series of electrical impulses. This would seem to imply an intact. structural membrane system that allows for cell depolarization and the release of intracellular cations that are converted into a contractile force. There was also response to chemical stimulation with both muscarinic or adrenergic agonists. This would imply a developing neurotransmitter receptor pathway. These findings are consistent with the functional profile seen in other tissues, such as bladder and urethra, where a response is seen to both electrical and chemical stimulation parameters after just a few weeks of tissue development (Chen et al. *World J Urol.* 18 (1): 67-70, (2000); Oberpenning et al. *Nature Biotech.* 17: 2 (1999)).

This study demonstrates that VE and SMC's can be reconstituted in the laboratory onto large polymer constructs for total vaginal replacement. This technology may have clinical advantages to those patients in the future requiring extensive lower genital reconstruction.

Example 4

Preparation of a Tissue Engineered Fallopian Tube

This example describes the use of fallopian tube epithelial and smooth muscle cells for the engineering of fallopian tubes in vivo.

Fallopian tube epithelial cells and smooth muscle cells of female rabbits can be grown and expanded in culture. Both cell types can be characterized immunocytochemically. Fallopian tube epithelial cells and smooth muscle cells can be seeded onto polymers of polyglocolic acid (PGA) at approx.

$10 \times 10^6$ cells/cm$^3$ and $20 \times 10^6$ cells/cm$^3$, respectively. The cell seeded scaffolds can be subcutaneously implanted into nude mice, which can be sacrificed at 1, 4, and 6 weeks after implantation. Immunocytochemical and histochemical analyses can be performed with pancytokeratins AE1/AE3, and smooth muscle specific alpha-actin antibodies to confirm the reconstituted tissue phenotype. Western blot analyses and electrical field stimulation studies can also performed to further characterize the tissue engineered constructs both at a molecular and functional level.

The example demonstrates that fallopian tube epithelial cells and smooth muscle cells can be cultured and expanded in vitro. Cell seeded polymer scaffolds can form vascularized fallopian tube tissue in vivo that have similar phenotypic and functional properties to normal fallopian tube tissues.

Example 5

Materials and Methods for Creating an Artificial Uterus (i) Cell Harvest and Culture Twelve New Zealand white rabbits weighing 3.5 to 4.0 kg were anesthetized with intramuscular injections of ketamine (25 mg/kg) and xylazine (5 mg/kg), and maintained by isoflurane (1-3%). After exposure of a uterine horn, a 1×1 cm segment of uterine tissue was excised from each animal. The mucosal tissue was digested with 0.1% collagenase type IV (Worthington, Lakewood, N.J.) in a 37° C. shaking incubator for 40 minutes. Subsequently, the mucosal tissue was rinsed and the cells were plated on a 6-well culture dish in culture medium, consisting of F-12 (Gibco, Grand Island, N.Y.) and Dulbecco's modified Eagle's medium (Mediatech, Herndon, Va.; F-12/DMEM, v/v 1:1) supplemented with EGF (5 ng/ml), bovine pituitary extract (40 ng/ml) and 10% fetal bovine serum (Gemini, Woodland, Calif.) (Baez, C. E., Atala, A.: Uterus. In: *Methods of Tissue Engineering*. Edited by A. Atala and R. P. Lanza. Boston: Academic Press, pp. 1189-1194, 2002); (Mulholland et al. Changes in proteins synthesized by rabbit endometrial epithelial cells following primary culture. *Cell Tissue Res*, 252: 123, 1988); (Vigano et al.: Culture of human endometrial cells: a new simple technique to completely separate epithelial glands. *Acta Obstet Gynecol Scand*, 72: 87, 1993); (Bongso et al.: Establishment of human endometrial cell cultures. *Hum Repro*, 3: 705, 1988)).

The tissue specimens were dissected under sterile conditions, and the epithelial and muscular layers were separated. The muscle tissue was minced with sharp scissors into fragments sized less than 2 mm$^3$, and placed on culture plates. Muscle cell culture medium, consisting of DMEM supplemented with 10% FBS, was gently added and the cultures were placed in a humidified incubator with 5% CO$_2$ until confluent (Merviel et al.: Normal human endometrial cells in culture: characterization and immortalization of epithelial and stromal cells by SV 40 large T antigen. *Biol Cell*, 84: 187, 1995); (Osteen et al.: Development of a method to isolate and culture highly purified populations of stromal and epithelial cells from human endometrial biopsy specimens. *Fertil Steril*, 52: 965, 1989). The medium was changed every 3 days and the cells were subcultured with 0.5% trypsin (Sigma, St. Louis, Mo.). Both epithelial and smooth muscle cells were expanded separately until sufficient cells were available.

(ii) Polymer Scaffolds

Non-woven meshes of polyglycolic acid (PGA, bulk density of 58 mg/cc, Albany International, Mansfield, Mass.) sized 6 cm×3 cm were configured into a uterus shaped mold using 5-0 absorbable sutures. The biodegradable polymer meshes were composed of 15 μm fibers with an interfiber distance of 100-200 μm and a porosity of 95%. The constructs were coated with poly-DL-lactide-co-glycolide (PLGA, 50:50; Sigma Chemical, St. Louis, Mo.) in chloroform (5% w/v) in order to increase stiffness and maintain its circumferential structure. The solvent was subsequently allowed to evaporate, and the scaffolds were kept under vacuum for 2 days. The scaffolds were sterilized with ethylene oxide.

(iii) Cell Seeding

Primary uterine smooth muscle and epithelial cells were seeded on the tubular shaped polymers in a stepwise fashion. The smooth muscle cells were seeded initially at a concentration of $60 \times 10^6$ cells/ml. The cells were grown for 3 days in a humidified incubator with DMEM supplemented with 10% FBS. The medium was changed every 24 hours in order to ensure sufficient supply of nutrients. Subsequently, the epithelial cells were seeded at a concentration of $60 \times 10^6$ cells/ml. The seeded cells were incubated an additional 48 hours prior to implantation.

(iv) Surgery and Post-Operative Evaluation

Under anesthesia, a lower midline abdominal incision was made and both uterine horns were exposed in the twelve female rabbits that had the previous uterine biopsy (Millbrook farms, Concord, Mass.). Approximately 80% of the circumferential diameter of each unilateral uterine horn was excised, leaving a thin longitudinal strip. The excised uterine horns were replaced with the autologous cell-seeded constructs. The anastomoses between the constructs and the native ovaries and vaginas were performed through small tissue cuffs at each end using 6-0 Vicryl sutures. Non-absorbable marking sutures were placed at each anatomotic site for future identification. Polymers without cells and sham operated animals served as controls (n=3 per group). All the constructs were covered with omentum. Hysterosalpingography was performed at 1, 3 and 6 months after surgery in order to identify the structural integrity of the implanted constructs. The animals were sacrificed at 1, 3, and 6 months after surgery (n=3 per time point).

(v) Histological and Immunocytochemical Analyses

The retrieved uterine tissue specimens were formalin fixed, paraffin embedded, sectioned and stained histologically with hematoxylin and eosin, and Masson's trichrome. Immunocytochemical analyses were performed on cultured cells grown on chamber slides and on the retrieved specimens using specific antibodies. Uterine smooth muscle cells were labeled with monoclonal anti-α smooth muscle specific actin (Dako, Carpinteria, Calif.), uterine epithelial cells were labeled with Pancytokeratins AE1/AE3 (Dako, Carpinteria, Calif.), and estrogen receptor function was assayed with estrogen receptor β antibodies (Santa Cruz, Santa Cruz, Calif.) (Monje et al. Subcellular distribution of native estrogen receptor alpha and beta isoforms in rabbit uterus and ovary. *J Cell Biochem*, 82: 467, 2001). Immunolabeling was performed using the avidin-biotin detection system (Vector laboratories, Burlingame, Calif.). Sections were counterstained with Gill's hematoxylin.

(vi) Western Blot Analyses

Freshly obtained uterine tissue samples were homogenized and the proteins were prepared by routine protein extraction methods using lysis buffer containing 1× phosphate buffered saline, 0.5% sodium deoxycholate, 0.1% sodium dodecyl sufate (SDS), 10 μg/ml aprotinin and 10 μg/ml leupeptin. Insoluble materials were removed by centrifugation at 14,000 rpm for 20 minutes at 4° C. Protein concentration was determined with the Bio-Rad protein assay kit. An equal amount (20 µg) of each sample was diluted (1:1 volume) with 2× sample buffer (0.125M tris-HCl, pH 6.8, 4% SDS, 10% 2-mercaptoethanol, 20% glycerol and 0.004% bromophenol blue). Samples were boiled for 5 minutes and loaded onto 10% sodium dodecyl sulfate-plyacrylamide gels. After electrophoresis, proteins were transferred to polyvinylidine difluoride membranes with a Multiphore series semi-dry transfer unit (Pharmacia Biotech, Inc.). The membranes were blocked with 3% BSA (4.5 g BSA, 300 uL 10% NaAzide, 150 mL 1× TBS/T) for one hour and followed by incubation in a 1:1000 dilution of mouse anti-human AE1/AE3, α-actin and estrogen receptor primary bodies overnight at 4° C. The membranes were subsequently treated with secondary antibody conjugates for 1 hour at room temperature. Immunoblots were treated with an ECL kit (Amersham Life Sciences Inc., Illinois) and exposed to radiographic films for 1-10 minutes. The films were developed in an X-Omat machine.

(vii) Organ Bath Studies

Modified Krebs solution (NaCl 134 mmol, KCl 3.4 mmol, $CaCl_2$ 2.8 mmol, potassium phosphate monobasic 1.3 mmol, $NaHCO_3$ 16 mmol, $MgSO_4$ 0.6 mmol, and glucose 7.7 mmol) was used for the tissue bath studies (Piechota et al.: In vitro functional properties of the rat bladder regenerated by the bladder acellular matrix graft. *J Urol,* 159: 1717, 1998). The solution was maintained at pH 7.4 during all experiments by constant bubbling with 95% $O_2$/5% $CO_2$. The 50 ml double-chambered Quiet Bath (Radnoti Glass Technology, Monrovia, Calif.) was used as the working chamber. Continuous gas flow induced circulation of Krebs solution, which was warmed to 37° C. by an external heating circuit (Immersion Circulator, model 1112, VWR Scientific Product, West Chester, Pa.).

For tissue contraction, the uterine tissue strips (n=3 per animal) were immersed in the tissue baths to the vertical L-shaped tissue supporter with platinum iridium electrodes (10 mm diameter, separated by 20 mm). An isometric force displacement transducer (Radnoti Glass Technology, Monrovia, Calif.) was connected on the other side by means of two 5-0 braided silk sutures. A Grass 48 electric stimulator (Grass Technique, West Warwick, R.I.) was the source of electric field stimulation (EFS). The transducer signal was fed into a chart recorder (Econo-1325, Biorad, Hercules, Calif.). A 2.0 gm preload was applied twice at 15 minutes intervals. The strips were allowed to equilibrate for at least 30 minutes prior to the start of each experiment. For electric field stimulation studies, 100 volts; 1.0 ms pulse duration; 5, 10, 20, 40, 50 pulses per second (pps) frequency with 2-minute intervals between each stimulation were used. For pharmacological stimulation, contractility was examined using a muscarinic receptor agonist (carbachol, $1\times10^{-4}$M) and antagonist (atropine, $1\times10^{-4}$M), and an adrenergic receptor agonist (phenyephrine, $1\times10^{-4}$M) and antagonist (phentolamine, $1\times10^{-4}$M). The weight of the strips were measured after each contractility test. The contractile strength was expressed as gram force per 100 mg of tissue (g/100 mg). Organ bath studies were performed on the engineered and normal control uterine tissues.

(viii) Biomechanical Properties

Rectangular tissue strips (20 mm×4.5 mm×1.5 mm) were obtained from normal uteri, engineered uterine implants and scaffolds implanted without cells (n=5 per sample). Tensile tests (Instron model 5544, MA, USA) were performed by elongating the tissue strips longitudinally at a speed of 0.05 mm/second (Dahms et al.: Composition and biomechanical properties of the bladder acellular matrix graft: comparative analysis in rat, pig and human. *Br J Urol,* 82: 411, 1998). Stress/strain curves for each specimen were generated, and the maximum tensile strength and strain forces (MPa) were determined. The maximum tensile strain, which was determined in response to the ultimate strength, was calculated as the elongated displacement ratio to initial length. Statistical analysis was performed using the unpaired Student's t-test (InStat™, Graphpad Software Inc., San Diego, Calif.). A value of $p<0.05$ was considered to be statistically significant.

Example 6

Creating a Tissue Engineered Uterus Using Autologous Cells

This study demonstrates that uterine tissue can be formed using uterine epithelial and smooth muscle cells, e.g., myometrial cells, in vivo. The materials and methods are described in Example 5.

(i) Cell Culture.

Rabbit uterine epithelial and myometrial cells were reliably grown and expanded in culture. Microscopically, the epithelial and smooth muscle cells demonstrated the typical cobble stone appearance and elongated stromal-like appearance, respectively. Each cell type was phenotypically confirmed using pancytokeratins AE1/AE3, estrogen receptor β and smooth muscle specific α-actin antibodies, respectively. Western blot analyses of the uterine cells using the corresponding antibodies confirmed the cells protein expression.

(ii) Gross Examination

All animals survived until their pre-determined time points without demonstrating any untoward effects. The marking sutures, which identified the transition zone between the native and implanted tissues, were visualized in all the retrieved uterine tissue implants. Grossly, the cell-seeded uterine implants demonstrated well-defined uterine horns at all time points. The uterine tissue replaced with the cell-seeded constructs demonstrated well-defined uterine horns grossly at 1 month, 3 month and 6 months, respectively. All of the cell-seeded implants demonstrated a widely patent lumen. The interior lumen of the engineered uterine implants showed a mucosal surface, which could not be distinguished grossly from normal uterine mucosa. The lumen of the polymer matrices implanted without cells collapsed by 1 month and showed graft shrinkage with increasing fibrosis at 3 months and 6 months.

(iii) Radiographic Studies

Hysterosalpingograms of the cell-seeded constructs showed fully distensible patent tubular uterine structures at all time points. Hysterosalpingography of the cell seeded implants at 1 month and at 6 months were similar to the sham operated animals. The non-seeded constructs showed marked stenosis in the mid-segment of the uterus 1 month after surgery, and the lumens collapsed completely over time as demonstrated at 6 months.

(iv) Histological and Immunocytochemical Analyses

The uterine implants seeded with cells and retrieved at 1 month showed a thin layer of epithelial cells. Unorganized smooth muscle cell fibers and undegraded polymers were observed within the retrieved tissues. Morphologically normal uterine tissues, consisting of an endometrial cell lining surrounded by submucosa and muscle layers were detected by 3 months. The smooth muscle fibers organized and aligned to form muscle tissue bundles and a uniform layer of uterine epithelial cells were observed in all instances. The polymer fibers degraded completely by 3 months. Each cell type was confirmed immunocytochemically with specific antibodies to smooth muscle α-actin, pancytokeratins AE1/AE3 and estrogen receptor β ((Vigano et al.: *Acta Obstet Gynecol Scand*, 72: 87, 1993); (Bongso et al.: *Hum Repro*, 3: 705, 1988); (Merviel et al. *Biol Cell*, 84: 187, 1995)).

Uterine implants without cells showed a vast amount of fibroblast deposition and an extensive recruitment of inflammatory cells 1 month after surgery. Scattered epithelial islands, which stained positively with pancytokeratins AE1/AE3 antibodies, and unorganized smooth muscle α-actin positive cells were identified. At 3 and 6 months, the implants without cells demonstrated abundant connective tissue formation with a luminal epithelial layer but only scant, unorganized muscle fibers. The retrieved uterine implants demonstrated appropriate cellular organization. Cell phenotype was confirmed by immunostaining with α-actin and cytokeratins AE1/AE3 antibodies.

(v) Western Blot Analyses

The protein fractions from normal uterine tissue and the cell-seeded implants demonstrated the presence of similarly expressed 40-60 kDa cytokeratins AE1/AE3 and 42 kDa smooth muscle α-actin. Decreased expression of cytokeratins AE1/AE3 and α-actin were noted in the polymer-only implants. Expression of 50 kDa estrogen receptor β was detected in the protein fractions of the cell-seeded implants and normal uterine tissue, however, this protein was minimally expressed in the polymer-only implants.

(vi) Organ Bath Studies

Organ Bath Studies are shown in FIG. 2. The tissue engineered strips retrieved one month after implantation did not elicit a response to electric field or pharmacological stimulation. Tissue strips from the cell-seeded implants at 3 and 6 months showed contraction responses to electric field stimulation (FIG. 2D). The contraction amplitude of the cell-seeded uterine implants at 6 months was approximately 70% of the normal uterine tissues. The range of the maximal contraction strength varied from 3.7 to 8.7 g/100 mg. Most of the engineered tissue strips reached a maximum contractility at 40-50 Hz. The cell-seeded implants had a slower relaxation to baseline than normal uterine tissue. Normal uterine tissue response to electric field stimulation is shown in FIG. 2A and to pharmacological stimulation (carbachol (CA), atropine (AT), phenylephrine (PE), and phentolamine (PL)) is shown in FIGS. 2B and C. Pharmacological responses to muscarinic and adrenergic receptor agonists were also observed in the engineered uterine tissues at 3 and 6 months after retrieval (FIGS. 2E-F).

(vii) Biomechanical Properties

Figure 3A:
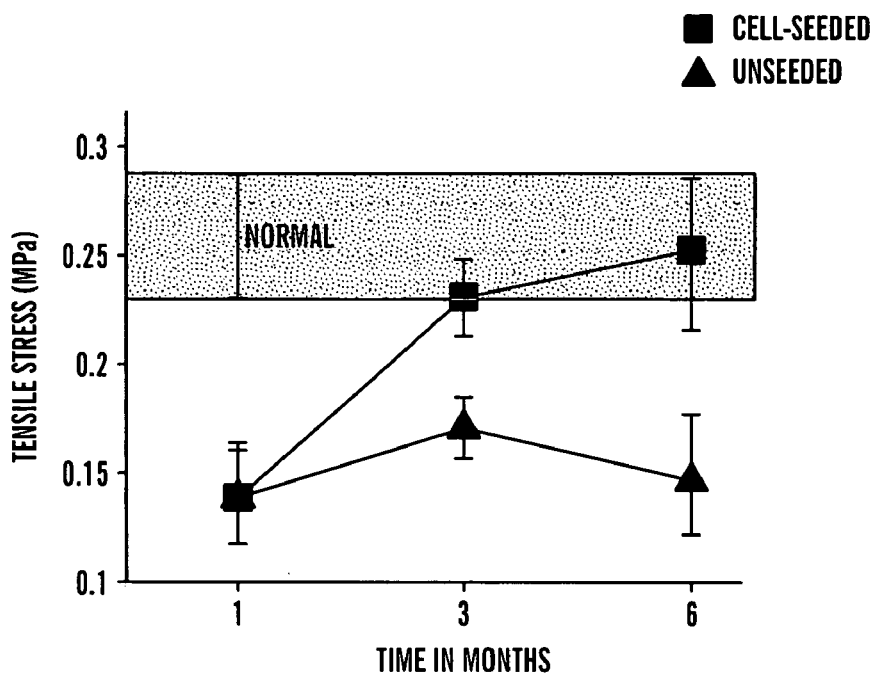
FIG. 3A is a graph showing the maximum tensile stress of uterine cell-seeded constructs at 1, 3, and 6 months after implantation.
Figure 3B:
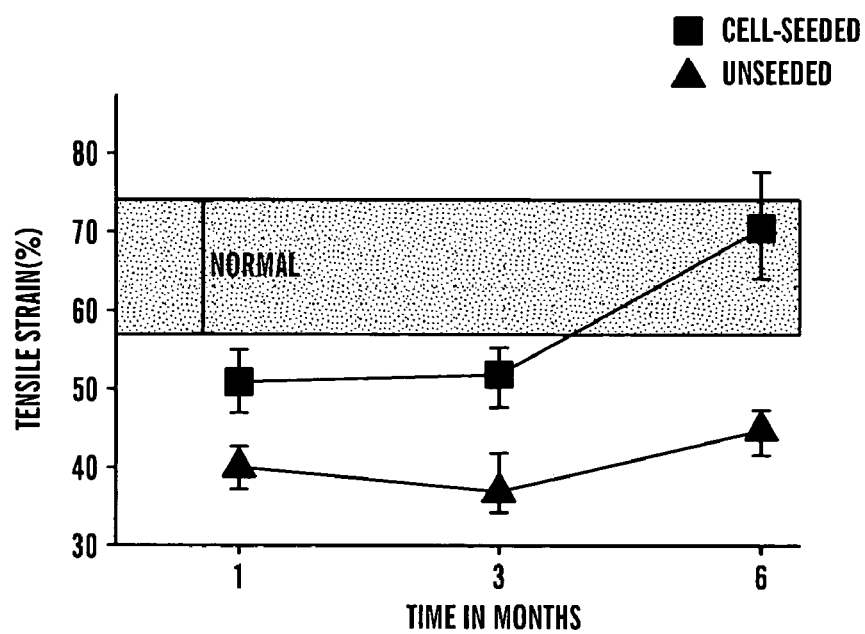
FIG. 3B is a graph showing the maximum tensile strain of uterine cell-seeded constructs at 1, 3, and 6 months after implantation.

The stress/strain properties of the cell-seeded uterine tissues were similar to the normal controls by 6 months after implantation. There was a significant difference in the maximum tensile stress noted between the cell-seeded uterine tissues (□) and the scaffold-only control (Δ) implants (0.25 and 0.23 vs 0.15 MPa) at 3 and 6 months (FIG. 3A). The mean maximum strain for the cell seeded implants (□) and the scaffold-only controls (Δ) were significantly different at 6 months (68% vs 38%) (FIG. 3B).

(viii) Overview

Using the methods and compositions of the present invention, uterine epithelial and muscle cells were harvested, grown, expanded and seeded onto pre-configured polymer scaffolds for uterine tissue replacement. The implanted uterine cells were able to survive, reorganize and formed spatially oriented multi-layered uterine tissue structures. The cells retained their phenotypic characteristics during the entire duration of the study. The uterine cells possessed estrogen receptors, as confirmed immunocytochemically and by Western blot analyses, which indicated their ability to respond to estrogen hormones.

The polymer scaffolds used in this study served as a cell delivery vehicle, which would maintain their structural integrity until mature tissues were formed. The cells were seeded onto pre-configured uterine shaped polymer scaffolds, which were designed to degrade by 3 months after implantation.

The engineered uterine constructs seeded with cells demonstrated structurally intact uterine tissues, as demonstrated by hysterosalpingography and gross examination. All of the implants without cells resulted in stricture formation initially which progressed until obstruction occurred. These findings indicate that scaffolds alone, without cells, are not sufficient for normal uterine tissue regeneration.

The uterine tissues created in this study demonstrated anatomical and histologic characteristics similar to those present in native uterine tissues, consisting of epithelial lined lumens, surrounded by stromal and muscle layers. Immunocytochemical and Western blot analyses using anti-pancytokeratin AE1/AE3 and anti-smooth muscle α-actin identified the epithelial and muscle phenotype and expression. Furthermore, estrogen receptor β expression was confirmed within the engineered uterine tissues (Cooke et al.: Restoration of normal morphology and estrogen responsiveness in culture vaginal and uterine epithelia transplanted with stroma. *Proc Natl Acad Sci USA*, 83: 2109, 1986); (Bowen et al. Characterization of a polarized porcine uterine epithelial model system. *Biol Reprod*, 55: 613, 1996); (Classen-Linke et al.: Establishment of human endometrial cell culture system and characterization of its polarized hormone responsive epithelial cells. *Cell Tissue Res*, 287: 171, 1997); (Glasser et al. Receptivity is a polarity dependent special function of hormonally regulated uterine epithelial cells. *Microsc Res Tech*, 25: 106, 1993)).

The physical properties of the engineered uterine tissues were similar to normal native tissues. The engineered uterine tissues possessed adequate tissue resistance and compliance. Contractility is one of the most important indicators of uterine tissue function. In the present study the engineered uterine tissues demonstrated a large degree of contraction and relaxation, in response to electric field stimulation and pharmacological agents.

This study demonstrates that the methods of the present invention using biodegradable polymers and autologous cells can be successfully employed for the creation of a uterus. This inventions can be used in patients requiring tissue for uterine reconstruction.

Equivalents

Those skilled in the art will appreciate, or be able to ascertain using no more than routine experimentation, further features and advantages of the invention based on the above-described embodiments. Accordingly, the invention is not to be limited by what has been particularly shown and described, except as indicated by the appended claims. All publications and references are herein expressly incorporated by reference in their entirety.

What is claimed is:

1. A method of constructing artificial uterine tissue comprising:
   providing a biocompatible matrix;
   perfusing one side of the biocompatible matrix with a first cell population comprising a uterine epithelial cell population and with a second cell population comprising a smooth muscle cell population; and culturing the cell populations in the biocompatible matrix; to thereby create an uterine tissue structure, or uterine segment that is the functional equivalent of normal uterine tissue.

2. The method of claim 1, wherein the method further comprises perfusing the biocompatible matrix with at least one additional cell population.

3. The method of claim 1, wherein the second cell population is a substantially homogenous smooth muscle cell population.

4. The method of claim 1, wherein the method further comprises selecting a biocompatible matrix that comprises a polymer.

5. The method of claim 1, wherein the method further comprises selecting a biocompatible matrix that comprises a decellularized structure.

6. The method of claim 1, wherein the biocompatible matrix is formed from at least one material selected from the group consisting of cellulose ether, cellulose, cellulosic ester, fluorinated polyethylene, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyglycolic acid, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, copolymers and physical blends thereof.

7. The method of claim 1, wherein the biocompatible matrix is polyglycolic acid (PGA).

* * * * *